United States Patent
Plowman et al.

(10) Patent No.: US 6,818,440 B2
(45) Date of Patent: Nov. 16, 2004

(54) DIAGNOSIS AND TREATMENT OF ALK-7 RELATED DISORDERS

(75) Inventors: Gregory D. Plowman, San Carlos, CA (US); Douglas Clary, San Francisco, CA (US)

(73) Assignee: Sugen, Inc., South San Francisco, CA (US)

( * ) Notice: Subject to any disclaimer, the term of this patent is extended or adjusted under 35 U.S.C. 154(b) by 20 days.

(21) Appl. No.: 09/069,228

(22) Filed: Apr. 27, 1998

(65) Prior Publication Data

US 2003/0073143 A1 Apr. 17, 2003

Related U.S. Application Data

(60) Provisional application No. 60/044,428, filed on Apr. 28, 1997.

(51) Int. Cl.$^7$ .................... C12N 15/63; C12N 15/70; C12N 15/74; C12N 15/79; C07H 21/04
(52) U.S. Cl. .................... 435/320.1; 435/252.3; 435/254.11; 435/325; 536/23.1; 536/23.4; 536/23.5
(58) Field of Search ................ 435/320.1, 252.3, 435/254.11, 325, 69.1, 70.1, 70.3, 71.1, 320; 536/23.1, 23.4, 23.5, 23.2, 24.1, 24.3

(56) References Cited

U.S. PATENT DOCUMENTS

| | | | |
|---|---|---|---|
| 4,343,940 A | | 8/1982 | Kreighbaum et al. |
| 4,376,110 A | | 3/1983 | David et al. |
| 4,447,608 A | | 5/1984 | Jones et al. |
| 4,757,072 A | | 7/1988 | Kabbe et al. |
| 4,945,050 A | | 7/1990 | Sanford et al. ......... 435/172.1 |
| 5,168,050 A | * | 12/1992 | Hammonds, Jr. et al. |
| 5,217,999 A | | 6/1993 | Levitzki et al. ............ 514/613 |
| 5,283,173 A | | 2/1994 | Fields et al. ................... 435/6 |
| 5,302,606 A | | 4/1994 | Spada et al. ................ 514/357 |
| 5,316,553 A | | 5/1994 | Kaul et al. ...................... 8/639 |
| 5,330,992 A | | 7/1994 | Eissenstat et al. .......... 514/312 |
| 5,602,171 A | | 2/1997 | Tang et al. ................. 514/455 |
| 5,614,609 A | * | 3/1997 | Ibanez et al. |
| 5,789,565 A | * | 8/1998 | Ibanez et al. |
| 5,811,245 A | * | 9/1998 | Ibanez et al. |

FOREIGN PATENT DOCUMENTS

| | | |
|---|---|---|
| EP | 0 520 722 A1 | 12/1992 |
| EP | 0 562 734 A1 | 9/1993 |
| EP | 0 566 226 A1 | 10/1993 |
| WO | 91/15495 | 10/1991 |
| WO | 92/20642 | 11/1992 |
| WO | 92/21660 | 12/1992 |
| WO | 93/09236 | 5/1993 |
| WO | 93/10242 | 5/1993 |
| WO | 94/01119 | 1/1994 |
| WO | 94/03427 | 2/1994 |
| WO | 94/14808 | 7/1994 |
| WO | 94/23039 | 10/1994 |
| WO | 95/06735 | 3/1995 |
| WO | 96/22976 | 8/1996 |
| WO | 96/34985 | 11/1996 |

OTHER PUBLICATIONS

The abstract of Voeikova et al, Biotekhnologiya, 1988, vol. 4, pp. 176–182.*
Verma et al (Nature, 1997, vol. 389, pp. 239–242).*
Eck et al (Gene–Based Therapy, In: The Pharmacological Basis of Therapeutics, Goodman and Gilman, Ed.s, 1996, pp. 77–101).*
Orkin et al ( "Report and Recommendation of the Panel to Assess the NIH Investment in Research on Gene Therapy", NIH, 1995).*
Houdebine, Journal of Biotechnology, 1994, vol. 34, pp. 269–287.*
Ryden, M. et al. A novel type I receptor serine–theronine kinase predominantly expressed in the adult central nervous system. J. Biol. Chem. vol. 271(48), pp. 30603–30609, Nov. 1996.*
Accession No. AR021339 on GenEmbl database, Dec. 1998.*
Abe et al., "Molecular Characterization of a Novel Metabotropic Glutamate Receptor mGluR5 Coupled to Inositol Pohosphate/$Ca^{2+}$Signal," *J. Biol. Chem.* 267(19):13361–13368 (1992).
Allen et al., "Modulation of CD4 by suramin," *Clin. Exp. Immunol.* 91:141–146 (1991).
Altschul et al., "Basic Local Alignment Search Tool," *J. Mol. Biol.* 215:403–410 (1990).
Anafi et al., "Tyrphostin–Induced Inhibition of $p210^{bcr-abl}$ Tyrosine Kinase Activity Induces K562 to Differentiate," *Blood* 82:3524–3529 (1993).
Ausubel et al., Index to *Current Protocols in Molecular Biology*.
Baker et al., "Induction of acetylcholine receptor clustering by native polystyrene beads," *Journal of Cell Science* 102:543–555 (1992).
Barker et al., "In vitro activity of non–glutamate containing quinazoline–based thymidylate synthase inhibitors," *Proceedings of the American Association for Cancer Research* 32:327 at abstract No. 1939 (1991).
Bassing et al., "A Transforming Growth Factor β Type I Receptor That Signals to Activate Gene Expression," *Science* 263:87 (1994).

(List continued on next page.)

*Primary Examiner*—Karen A. Canella
(74) *Attorney, Agent, or Firm*—Beth A. Burrous; Foley & Lardner LLP

(57) ABSTRACT

The present invention relates to ALK-7 polypeptides, nucleic acids encoding such polypeptides, cells, tissues and animals containing such nucleic acids, antibodies to such polypeptides, assays utilizing such polypeptides, and methods relating to all of the foregoing. Methods for treatment, diagnosis, and screening are provided for ALK-7 related diseases or conditions characterized by an abnormal interaction between an ALK-7 polypeptide and an ALK-7 binding partner.

19 Claims, No Drawings

OTHER PUBLICATIONS

Bayer et al., "The Avidin–Biotin Complex in Affinity Cytochemistry," *Meth. Enzym.* 62:308 (1979).

Benoist and Chambon, "In vivo sequence requirements of the SV40 early promoter region," *Nature* 290:304–310 (1981).

Bertino, "Toward Improved Selectivity in Cancer Chemotherapy: The Richard and Hinda Rosenthal Foundation Award Lecture," *Cancer Research* 39:293–304 (1979).

Bilder et al., "Tyrphostins inhibit PDGF–induced DNA synthesis and associated early events in smooth muscle cells," *Am. J. Physiol.* 260(Cell Physiol.29):C721–C730 (1991).

Bollon et al., "DNA Transformation Efficiency of Various Bacterial and Yeast Host–Vector Systems," *J. Clin. Hematol. Oncoll.* 10:39–48 (1980).

Botstein et al., "Making Mutations In Vitro and Putting Them Back Into Yeast," *Miami Wntr. Symp.* 19:265–274 (1982).

Brinster et al., "Factors Affecting the Efficiency of Introducing Foreign DNA into Mice by Microinjecting Eggs," *Proc. Natl. Acad. Sci. USA* 82:4438–4442 (1985).

Broach, "The Yeast Plasmid 2µ Circle," *Cell* 28:203–204 (1982).

Broach, *The Molecular Biology of the Yeast Saccharomyces: Life Cycle and Inheritance*, Cold Spring Harbor Laboratory, Cold Spring Harbor, NY, p. 445–470.

Brunton et al., "Anti–tumour activity of novel tryphostins in breast cancer cells," *Proceedings of the American Association for Cancer Research* 33:558 at abstract No. 3335 (1992).

Bryckaert et al., "Inhibition of Platelet–Derived Growth Factor–Induced Mitogenesis and Tyrosine Kinase Activity in Cultured Bone Marrow Fibroblasts by Tyrphostins," *Exp. Cell Research* 199:255–261 (1992).

Bullock et al., *Techniques in Immunocytochemistry*, Academic Press, Orlando, FL vol. 1 (1982), vol. 2 (1983), vol. 3 (1985).

Burke et al., "Arylamides of Hydroxylated Isoquinolines as Protein–Tyrosine Kinase Inhibitors," *Bioorganic & Medical Chemistry Letters* 2(12):1771–1774 (1992).

Burke et al., "Bicyclic Compounds as Ring–Constrained Inhibitors of Protein–Tyrosine Kinase p56$^{lck\ 1}$," *Journal of Medicinal Chemistry* 36(4):425–432 (1993).

Campbell, *Monoclonal Antibody Technology: Laboratory Techniques in Biochemistry and Molecular Biology*, Elsevier Science Publishers, Amsterdam, The Netherlands, (1984).

Capecchi MR, "High Efficiency by Direct Microinjection of DNA into Cultured Mammalian Cells," *Cell* 22:479–88 (1980).

Capecchi, "Altering the Genome by Homologous Recombination," *Science* 244:1288–1292 (1989).

Cenatiempo, "Prokaryotic Gene Expression In Vitro Transcription—Translation Coupled Systems," *Biochimie* 68:505–516 (1986).

Chard, "An Introduction to Radioimmunoassay and Related Techniques," Elsevier Science Publishers, Amsterdam, The Netherlands (1986).

Chater et al., *Sixth International Symposium on Actinomycetales Biology*, Akademiai Kaido, Budapest, Hungary, pp. 45–54 (1986).

Chen and Okayama, "High–Efficiency Transformation of Mammalian Cells by Plasmid DNA," *Molecular and Cellular Biology* 7(8):2745–2752 (1987).

Chomczynski and Sacchi, "Single–Step Method of RNA Isolation by Acid Guanidinium Thiocyanate–Phenol–Chloroform Extraction," *Analytical Biochemistry* 162:156–159 (1987).

Chu G., et al., "Electroporation for the Efficient Transfection of Mammalian Cells with DNA," *Nucleic Acids Res.*, 15:1311–26 (1987).

Curiel et al., "Adenovirus Enhancement of Transferrin–Polylysine–Mediated Gene Delivery," *Proc. Natl. Acad. Sci. USA* 88:8850–8854 (Oct., 1991).

Curiel et al., "Gene Transfer to Respiratory Epithelial Cells via the Receptor–mediated Endocytosis Pathway," *Am. J. Respir. Cell. Mol. Biol.* 6:247–252 (1992).

Curtin et al., "Inhibition of the growth of human hepatocellular carcinoma in vitro and in athymic mice by a quinazoline inhibitor of thymidylate synthase, CB3717," *Br. J. Cancer* 53:361–368 (1986).

Dijke et al., "Activin Receptor–like Kinases: A Novel Subclass of Cell–Surface Receptors with Predicted Serine/Threonine Kinase Activity," *Oncogene* 8:2879 (1993).

Dolle et al., "5,7–Dimethoxy–3–(4–pyridinyl)quinoline is a Potent and Selective Inhibitor of Human Vascular–Type Platelet–Derived Growth Factor Receptor Tyrosine Kinase," *J. Med. Chem.* 37:2627–2629 (1994).

Dong et al., "Activation of tumoricidal properties in macrophages by lipopolysaccharide requires protein–tyrosine kinase activity," *Journal of Leukocyte Biology* 53:53–60 (1993).

Dong et al., "Protein Tyrosine Kinase Inhibitors Decrease Induction of Nitric Oxide Synthase Activity in Lipopolysaccharide–Responsive and Lipopolysaccharide–Nonresponsive Murine Macrophages," *The Journal of Immunology* 151(5):2717–2724 (1993).

Engvall et al., "Enzyme–Linked Immunosorbent Assay, Elisa," *Immunot* 109:129 (1972).

Felgner and Ringold, "Cationic liposome–mediated transfection," *Nature* 337:387–388 (1989).

Felgner et al., "Lipofection: A Highly Efficient, Lipid–mediated DNA–transfection Procedure," *Proc. Natl. Acad. Sci. USA* 84:7413–7417 (1987).

Fernandes et al., "Biochemical and Antitumor Effects of 5,8–Dideazaisopteroylglutamate, a Unique Quinazoline Inhibitor of Thymidylate," *Cancer Research* 43:1117–1123 (1983).

Ferris et al., "Synthesis of Quinazoline Nucleosides from Ribose and Anthranilonitrile. Application of Phase–Transfer Catalysis in Nucleoside Synthesis," *J. Org. Chem.* 44(2):173–178 (1979).

Fields et al., "Cell Surface Markers for Distinguishing Different Types of Rat Dorsal Root Ganglion Cells in Culture," *Cell* 14:43 (1978).

Fingl and Woodbury, "Chapter 1—General Principles," in *The Pharmacological Basis of Therapeutics* 5th edition, Goodman and Gilman editors, MacMillan Publishing Co., Inc., New York, pp. 1–46 (1975).

Franzen et al., "Cloning of a TGFβ Type I Receptor That Forms a Heteromeric Complex with the TGFβ Type II Receptor," *Cell* 75(4):681 (1993).

Fry et al., "A Specific Inhibitor of the Epidermal Growth Factor Receptor Tyrosine Kinase," *Science* 265:1093–1095 (1994).

Gazit et al., "Tyrphostins 1. Synthesis and Biological Activity of Protein Tyrosine Kinase Inhibitors," *J. Med. Chem.* 32:2344–2352 (1989).

Gazit et al., "Tyrophostins. 3. Structure–Activity Relationship Studies of a —Substituted Benzylidenemalononitrile 5–S–Aryltyrphostins," *J. Med. Chem.* 36:3556–3564 (1993).

Gilman et al., "Isolation of Sigma–28–Specific Promoters from *Bacillus Subtilis* DNA," *Gene* 32:11–20 (1984).

Glick, "Factors Affecting the Expression of Foreign Proteins in *Escherichia Coli*," *J. Ind. Microbiot.* 1:277–282 (1987).

Goding, "Conjugation of Antibodies with Fluorochromes: Modifications to the Standard Methods," *J. Immunological Methods* 13:215–226 (1976).

Gold et al., "Translational Initiation in Prokaryotes," *Ann. Rev. Microbiol.* 35:365–404 (1981).

Gottesman, "Bacterial Regulation: Global Regulatory Networks," *Ann. Rev. Genet.* 18:415–441 (1984).

Graham et al., "Characteristics of a Human Cell Line Transformed by DNA from Human Adenovirus Type 5," *J. of Gen. Virology* 36:59–72 (1977).

Greene et al., "PC12 Pheochromocytoma Cells: Culture, Nerve Growth Factor Treatment, and Experimental Exploitation," *Methods Enzymol.* 147:207 (1987).

Hamer et al., "Regulation In Vivo of a Cloned Mammalian Gene: Cadmium Induces the Transcription of a Mouse Metallothionein Gene in SV$) Vectors," *J. Mol. Appl. Gen.* 1:273–288 (1982).

Hammer et al., "Spontaneous Inflammatory Disease in Transgenic Rats Expressing HLA–B27 and Human $_2$m: An Animal Model of HLA–B27–Associated Human Disorders," *Cell* 63:1099–1112 (1990).

Hanks and Hunter, "The Eukaryotic Protein Kinase Superfamily: Kinase (Catalytic) Domain Structure and Classification," *FASEB J* 9:576–595 (1995).

Hartmann et al., "Predicting the Orientation of Eukaryotic Membrane–Spanning Proteins," *Proc. Natl. Acad. Sci. USA*, 86:5786 (1989).

Haslam et al., "Pleckstrin Domain Homology," *Nature* 363:309 (1993).

Hawrot and Patterson, "Long–Term Culture of Dissociated Sympathetic Neurons," in *Methods in Enzymology—Cell Culture*, Jakoby and Pastan eds., Academic Press, New York, New York (1979), pp. 574–584.

Heldin, "Dimerization of Cell Surface Receptors in Signal Transduction," *Cell* 80:213–233 (1995).

Houdebine and Chourrout, "Transgenesis in Fish," *Experientia* 47:891–897 (1991).

Hurby et al., in *Synthetic Peptides: A User's Guide*, edited by Grant Washington University School of Medicine, W.H. Freeman and Company, New York, pp. 289–307.

Innis et al., *PCR Protocols: A Guide to Methods and Applications*, edited by Michael A. Innis et al., Academic Press, San Diego (1990) (Table of Contents Only).

Izaki, *Jpn. J. Bacteriol.* 33:729–742 (1978).

Jackman, "ICI D1694, a Quinazoline Antifolate Thymidylate Synthase Inhibitor That Is a Potent Inhibitor of L1210 Tumor Cell Growth in Vitro and in Vivo: A New Agent for Clinical Study," *Cancer Research* 51:5579–5586 (1991).

Jakoby et al., *Meth. Enzym.* 34:Index (1974).

Jasny, "Insect Viruses Invade Biotechnology," *Science* 238:1653 (1987).

John et al., "Plasmids as Epidemiologic Markers in Nosocomial Gram–Negative *Bacilli*: Experience at a University and Review of the Literature," *Rev. Infect. Dis.* 8:693–704 (1986).

Johnston and Hopper, "Isolation of the yeast regulatory gene GAL4 and analysis of its dosage effects on the galatose/melibiose region," *Proc. Natl. Acad. Sci. USA* 79:6971–6975 (1982).

Jones et al., "Quinazoline Antifolates Inhibiting Thymidylate Synthase: Varation of the Amino Acid," *J. Med. Chem.* 29:1114–1118 (1986).

Joyner et al., "Production of a mutation in mouse En–2 gene by homologous recombination in embryonic stem cells," *Nature* 338:153–156 (1989).

Kasprzak et al., "Location of a Contact Site Between Actin and Myosin in the Three–Dimensional Structure of the Acto–S1 Complex," *Biochemistry* 28:9230–8 (1989).

Kaur, "Tyrphostin induced growth inhibition: correlation with effect on $p210^{bcr-abl}$ autokinase activity in K562 chronic myelogenous leukemia," *Anti–Cancer Drugs* 5:213–222 (1994).

Kendall et al., "Plasmid Transfer in Streptomyces Lividans: Identification of a kil–kor System Associated with the Transfer Region of pIJ101," *J. Bacteriol.* 169:4177–4183 (1987).

King et al., "Site–specific dephosphorylation and deactivation of the human insulin receptor tyrosine kinase by particulate and soluble phosphotyrosyl protein phosphatases," *Biochem. J.* 275:413–418 (1991).

Klein, et al., "The Detection and Classification of Membrane–Spanning Proteins," *Biochim. Biophys. Acta* 815:468 (1985).

Köhler (Kohler) and Milstein, "Continuous cultures of fused cells secreting antibody of predefined specificity," *Nature* 256:495–497 (1975).

Kuo et al., "Effects of signalling transduction modulators on the transformed phenotypes in v–H–ras–transformed NIH 3T3 cells," *Cancer Letters* 74:197–202 (1993).

Lee and Skibo, "Active–Site–Directed Reductive Alkylation of Xanthine Oxidase by Imidazo[4,5–g]quinazoline–4,9–diones Functionalized with a Leaving Group," *Biochemistry* 26:7355–7362 (1987).

Lemus et al., "Studies of Extended Quinone Methides. Synthesis and Physical Studies of Purine–like Monofunctional and Bifunctional Imidazo[4,5–g]quinazoline Reductive Alkylating Agents," *J. Org. Chem.* 54:3611–3618 (1989).

Levitzki, "Tyrphostins: tyrosine kinase blockers as novel antiproliferative agents and dissectors of signal transduction," *FASEB J.* 6:3275–3282 (1992).

Ley and Seng, "Synthesis Using Benzofuroxan," *Synthesis* 1975:415–422 (1975).

Lutz et al., "The Distribution of Two hnRNP–Associated Proteins Defined by a Monoclonal Antibody Is Altered in Heat–Shocked HeLa Cells," *Experimental Cell Research* 175:109–124 (1988).

Lyall et al., "Tyrphostins Inhibit Epidermal Growth Factor (EGF)–Receptor Tyrosine Kinase Activity in Living Cells and EGF–stimulated Cell Proliferation," *J. Biol. Chem.* 264:14503–14509 (1989).

Maguire et al., "A new series of PDGF Receptor Tyrosine Kinase Inhibitors: 3–Substituted Quinoline Derivatives," *J. Med. Chem.* 37:2129–2137 (1994).

Maniatis, "Chapter 11: Recombinant DNA Procedures in the Study of Eukaryotic Genes," In: *Cell Biology: A Comprehensive Treatise, vol. 3 Gene Sequences Expression*, Academic Press, NY, pp. 563–608 (1980).

Massague, "The TGF–β Family and its Composite Receptors," *Trends Cell Biol.* 4:172 (1994).

Maxwell et al., "$^{19}$F Nuclear Magnetic Resonance Imaging of Drug Distribution in Vivo: The Diposition of an Antifolate Anticancer Drug in Mice," *Magnetic Resonance in Medicine* 17:189–196 (1991).

Mayer et al., "A novel viral oncogene with structural similarity to phospholipase C," *Nature* 332:272–275 (1988).

McGeoch, "On the Predictive Recognition of Signal Peptide Sequences," *Virus Research* 3:271 (1985).

McKnight, "Functional Relationships between Transcriptional Control Signals of the Thymidine Kinase Gene of Herpes Simplex Virus," *Cells* 31:355–365 (1982).

Millauer et al., "Glioblastoma growth inhibited in vivo by a dominant–negative Flk–1 mutant," *Nature* 367:576–579 (1994).

Miller et al., *Genetic Engineering*, Setlow, J. K., et al., eds., Plenum, vol. 8, pp. 277–297 (1986).

Miller, "Human gene therapy comes of age," *Nature* 357:455–460 (1992).

Mini et al., "Cytotoxic Effects of Folate Antagonists against Methotrexate–resistant Human Leukemic Lymphoblast CCRF–CEM Cell Lines," *Cancer Research* 45:325–330 (1985).

Mulligan, "The Basic Science of Gene Therapy," *Science* 260:926–932 (1993).

Nelson, "Detection of Acridinium Esters by Chemiluminescence," *Nonisotopic DNA Probe Techniques*, ed. Larry J. Kricka, (San Diego: Academic Press, Inc.) pp. 275–310 (1992).

Okayama, "A cDNA Cloning Vector That Permits Expression of cDNA Inserts in Mammalian Cells," *Molec. Cell. Bio.* 3:280 (1983).

Pati, "Novel vectors for expression of cDNA encoding epitope–tagged proteins in mammalian cells," *Gene* 114:285–288 (1992).

Pawson and Schlessinger, "SH2 and SH3 domains," *Current Biology* 3(7):434–442 (1993).

Peterson and Barnes, "Genistein and Biochanin A Inhibit the Growth of Human Prostate Cancer Cells but not Epidermal Growth Factor Receptor Tyrosine Autophosphorylation," *The Prostate* 22:335–345 (1993).

Phillips and Castle, "Quino[1,2–c]quinazolines. I. Synthesis of Quino[1,2–c]quinazolinium Derivatives and the Related Indazolo[2,3–α]quinoline Derivatives as Analogs of the Autitumor Benzo[c]phenanthridine Alkaloids," *J. Heterocyclic Chemistry* 17:1489–1496 (1980).

Pillemer et al., "Insulin Dependence of Murine Lymphoid T–Cell Leukemia," *Int. J. Cancer* 50:80–85 (1992).

Ponting, "Pleckstrin's Repeat Performance: A Novel Domain in G–protein Signaling," *TIBS* 21:245 (1996).

Posner et al., "Kinetics of Inhibition by Tyrphostins of the Tyrosine Kinase Activity of the Epidermal Growth Factor Receptor and Analysis by a New Computer Program," *Molecular Pharmacology* 45:673–683 (1993).

Pursel et al., "Genetic Engineering of Livestock," *Science* 244:1281–1288 (1989).

Reece et al., "Pharmacokinetics of Trimetrexate Administered by Five–Day Continuous Infusion to Patients with Advanced Cancer," *Cancer Research* 47:2996–2999 (1987).

*Remington's Pharmaceutical Sciences*, 1990, 18th ed., Mack Publishing Co., Easton, PA.

Rendu et al., "Inhibition of Platelet Activation by Tyrosine Kinase Inhibitors," *Biochemical Pharmacology* 44(5):881–888 (1992).

Robertson, E.J., ed., *Teratocarcinomas and Embryonic Stem Cells, A Practical Approach*, IRL Press, 1987 (Table of Contents Only).

Rubin, "*Drosophila Melanogaster* as an Experimental Organism," *Science* 240:1453–1459 (1988).

Ryden et al., "A Novel Type I Receptor Serine–Theronine Kinase Predominantly Expressed in the Adult Central Nervous System," *J. Biol. Chem.* 271:30603 (1996).

Sadowski et al., A Noncatalytic Domain Conserved among Cytoplasmic Protein—Tyrosine Kinases Modifies the Kinase Function and Transforming Activity of Fujinami Sarcoma Virus P130$^{gag-fps}$, *Molecular and Cellular Biology* 6(12):4396–4408 (1986).

Sambrook et al., *Molecular Cloning: A Laboratory Manual*, $2^{nd}$ Edition, Cold Spring Harbor Press (1989) (Table of Contents for vols. 1,2 and 3).

Sauro and Thomas, "Decreased Sensitivity of Aorta from Hypertensive Rats to Vasorelaxation by Tyrphostin," *Life Sciences* 53:PL371–376 (1993).

Sauro and Thomas, "Tyrphostin Attenuates Platelet–Derived Growth Factor–Induced Contraction in Aortic Smooth Muscle Through Inhibition of Protein Tyrosine Kinase(s)," *The Journal of Pharamacology and Experimental Therapeutics* 267:1119–1125 (1993).

Sculier et al., "Role of an Intensive Care Unit (ICU) in a Medical Onocology Department," *Cancer Immunol. and Immunotherapy* 23:A65 at abstract No. 257 (1986).

Shimoda et al, "A High Percentage Yeild of Tyrosine Hydroxylase–positive Cells from Rat E14 Mesencephalic Cell Culture," *Brain Research* 586:319–331 (1992).

Sikora and Grzelakowska–Sztabert, "Quinazoline CB 3717 and CB 3703 Inhibitors of Folate Retention and Metabolism in Ehrlich Ascites Carcinoma Cells and Some Organs of the Host–Mouse," *Cancer Letters* 23:289–295 (1984).

Sikora et al., "Development of an Assay for the Estimation of $N^{10}$–Propargyl–5,8–dideazafolic Acid Polyglutamates in Tumor Cells," *Analytical Biochemistry* 172:344–355 (1988).

Silver et al., "Amino terminus of the yeast GAL4 gene product is sufficient for nuclear localization," *Proc. Natl. Acad. Sci. USA* 81:5951–5955 (1984).

Simons et al., "Gene Transfer into Sheep," *Bio/Technology* 6:179–183 (1988).

Singer, S.J., "The Structure and Insertion of Integral Proteins in Membranes," *Ann. Rev. Cell Biol.* 6:247 (1990).

St. Groth et al., "Production of Monoclonal Antibodies: Strategy and Tactics," *J. Immunol. Methods* 35:1–21 (1980).

Stemberger et al., "The Unlabeled Antibody Enzyme Method of Immunohistochemistry," *J. Histochem. Cytochem.* 18:315 (1970).

Tabor et al., "DNA sequence analysis with a modified bacteriophage T7 DNA polymerase," *Proc. Natl. Acad. Sci. USA* 84:4767–4771 (1987).

Tijssen, "Practice and Theory of Enzyme Immunoassays: Laboratory Techniques in Biochemistry and Molecular Biology," Elsevier Science Publishers, Amsterdam, The Netherlands (1985).

Tsuchida et al., "Molecular Cloning of a Novel Type I Receptor Serine/Theonine Kinase for the TGFβ Superfamily from Rat Brain," *Molec. Cell. Neurosci.* 7:467 (1996).

Ulmanen et al., "Transcription and Translation of Foreign Genes in *Bacillus Subtillis* by the Aid of a Secretion Vector," *J. Bacteriol.* 162:176–182 (1985).

von Heijne, "A Method for Predicting Signal Sequence Cleavage Sites," *Nucleic Acids Research* 14(11):4683–4691 (1986).

Ward et al., "Construction and Characterisation of a Series of Multi–copy Promoter–probe Plasmid Vectors for Streptomyces Using the Aminoglycoside Phosphotransferase Gene From Tn5 as Indicator," *Mol. Gen. Genet.* 203:468–478 (1986).

Weir et al., *Handbook of Experimental Immunology*, 4th Ed., Blackwell Scientific Publications, Oxford, England, Chapter 10, (1986).

Wolbring et al., "Inhibition of GTP–utilizing Enzymes by Tyrphostins," *J. Biol. Chem.* 269:22470–22472 (1994).

Wrana et al., "Mechanism of Activation of the TGF–β Receptor," *Nature* 370:341–347 (1994).

Yang et al., "In Vivo and In Vitro Gene Transfer to Mammalian Somatic Cells by Particle Bombardment," *Proc. Natl. Acad. Sci. USA* 87:9568–9572 (1990).

Yoneda et al., "The Antiproliferative Effects of Tyrosine Kinase Inhibitors Tyrphostins on a Human Squamous Cell Carcinoma in Vitro and in Nude Mice," *Cancer Research* 51:4430–4435 (1991).

Aoki, N., et al., "The Novel Protein–Tyrosine Phosphatase PTP20 is a Positive Regulator of PC12 Cell Neuronal Differentiation," J. Biol. Chem. 271(46):29422–29426 (1996).

Maekawa K., et al., "Molecular Cloning of A Novel Protein–Tyrosine Phosphatase Containing a Membrane–Binding Domain and glgf Repeats," *FEBS Letters* 337:200–206 (1994).

Matthews, R. J., et al., "Characterization of Hematopoietic Intracellular Protein Tyrosine Phosphatases: Description of a Phosphatase Containing an SH2 Domain and Another Enriched in Proline–, Glutamic Acid–, Serine–, and Threonine–rich Sequences," *Mol. Cell. Biol.* 12(5):2396–2405 (1992).

Saras, J., et al., "Cloning and Characterization of PTPL1, A Protein Tyrosine Phosphatase with Similarities to Cytoskeletal–Associated Proteins," *J. Biol. Chem.* 269(39):24082–24089 (1994).

Stausberg, Robert, "National Cancer Institute, Cancer Genome Anatomy Project," *EMBL Database*, entry HS1185621; accession No. AA281242, (1997).

* cited by examiner

DIAGNOSIS AND TREATMENT OF ALK-7 RELATED DISORDERS

RELATED APPLICATIONS

This application relates to the U.S. Provisional Patent Application No. 60/044,428, by Plowman et al., entitled "Diagnosis and Treatment of ALK-7 Related Disorders," and filed Apr. 28, 1997.

FIELD OF THE INVENTION

The present invention relates to serine-threonine kinases. In particular, the invention concerns a protein termed ALK-7, nucleotide sequences encoding ALK-7, and various products and assay methods that can be used for identifying compounds useful for the diagnosis and treatment of various ALK-7-related diseases and conditions, for example neurological disorders.

BACKGROUND OF THE INVENTION

The following description is provided to aid in understanding the invention but is not admitted to be prior art to the invention.

Cellular signal transduction is a fundamental mechanism whereby external stimuli that regulate diverse cellular processes are relayed to the interior of cells. One of the key biochemical mechanisms of signal transduction involves the reversible phosphorylation of proteins, which enables regulation of the activity of mature proteins by altering their structure and function.

Protein kinases are one of the largest families of eukaryotic proteins with several hundred known members. These proteins share a 250–300 amino acid domain that can be subdivided into 12 distinct subdomains that comprise the common catalytic core structure. (Hanks and Hunter, *FASEB J.* 9:576–595, 1995) These conserved protein motifs have recently been exploited using PCR-based cloning strategies leading to a significant expansion of the known kinases. Multiple alignment of the sequences in the catalytic domain of protein kinases and subsequent phylogenetic analysis permits their segregation into a phylogenetic tree. In this manner, related kinases are clustered into distinct branches or subfamilies including: tyrosine kinases, cyclic-nucleotide-dependent kinases, calcium/calmodulin kinases, cyclin-dependent kinases and MAP-kinases, serine-threonine kinases and several other less defined subfamilies.

Protein kinases can also be characterized by their location within the cell. Some kinases are transmembrane receptor-type proteins capable of directly altering their catalytic activity in response to the external environment such as the binding of a ligand. Others are non-receptor-type proteins lacking any transmembrane domain. They can be found in a variety of cellular compartments from the inner surface of the cell membrane to the nucleus.

Many kinases are involved in regulatory cascades wherein their substrates may include other kinases whose activities are regulated by their phosphorylation state. Ultimately the activity of some downstream effector is modulated by phosphorylation resulting from activation of such a pathway.

The serine-threonine kinase (STK) receptor family can be divided into two related subgroups, type I and type II STK receptors. Whereas the type I receptors are unable to directly bind ligand, the type II receptors directly bind to various members of the transforming growth factor beta (TGFβ) superfamily which includes TGFβs, activins, bone morphogenic proteins (BMPs), growth and differentiation factors (GDFs), VG1-related, glial derived neurotrophic factors (GDNFs), activins, and inhibins. These ligands have diverse biologic roles that include: mesenchymal cell growth and differentiation, angiogenesis, embryogenesis and pattern formation, bone and cartilage growth, muscle and fat differentiation, hematopoiesis, inhibition of epithelial cell growth, and wound repair and scar formation. In addition, several TGFβ-family ligands are expressed in the nervous system where they control survival and proliferation of neuronal cells in development and in response to injury.

Functional STK receptor complexes are ligand-induced heterotetromers comprised of two type I and two type II proteins. Both type I and type II receptors have small cysteine-rich extracellular domains and intracellular catalytic domains. Type I receptors all have a characteristic region rich in glycine and serine residues (the GS domain) located in their intracellular juxtamembrane domain.

A model for STK receptor activation has been proposed through studies of TGFβ binding (Wrana, et al., *Nature*, 370:341–347, 1994). Ligand binds to a type II receptor dimer which in turn recruits type I receptor, which cannot bind ligand absent the type II receptor. The type I receptor is subsequently cross-phosphorylated on serine residues in the GS domain and on a conserved threonine residue just N-terminal to its cytoplasmic kinase domain. This phosphorylation activates the Type I receptor, resulting in propagation of the signal to downstream targets. (See C-H Heldin, *Cell* 80:213–223, 1995.)

SUMMARY OF THE INVENTION

The present invention concerns ALK-7 polypeptides, nucleic acids encoding such polypeptides, cells, tissues and animals containing such nucleic acids, antibodies to the polypeptides, assays utilizing the polypeptides, and methods relating to all of the foregoing.

A first aspect of the invention features an isolated, enriched, or purified nucleic acid molecule encoding an ALK-7 polypeptide.

By "isolated" in reference to nucleic acid is meant a polymer of 14, 17, 21 or more nucleotides conjugated to each other, including DNA or RNA that is isolated from a natural source or that is synthesized. The isolated nucleic acid of the present invention is unique in the sense that it is not found in a pure or separated state in nature. Use of the term "isolated" indicates that a naturally occurring sequence has been removed from its normal cellular (i.e., chromosomal) environment. Thus, the sequence may be in a cell-free solution or placed in a different cellular environment. The term does not imply that the sequence is the only nucleotide sequence present, but that it is essentially free (about 90–95% pure at least) of non-nucleotide material naturally associated with it and thus is meant to be distinguished from isolated chromosomes.

By the use of the term "enriched" in reference to nucleic acid is meant that the specific DNA or RNA sequence constitutes a significantly higher fraction (2–5 fold) of the total DNA or RNA present in the cells or solution of interest than in normal or diseased cells or in the cells from which the sequence was taken. This could be caused by a person by preferential reduction in the amount of other DNA or RNA present, or by a preferential increase in the amount of the specific DNA or RNA sequence, or by a combination of the two. However, it should be noted that "enriched" does not imply that there are no other DNA or RNA sequences present, just that the relative amount of the sequence of interest has been significantly increased.

The term "significant" here is used to indicate that the level of increase is useful to the person making such an increase, and generally means an increase relative to other nucleic acids of about at least 2 fold, more preferably at least 5 to 10 fold or even more. The term also does not imply that there is no DNA or RNA from other sources. The other source DNA may, for example, comprise DNA from a yeast or bacterial genome, or a cloning vector such as pUC19. This term distinguishes the sequence from naturally occurring enrichment events, such as viral infection, or tumor type growths, in which the level of one mRNA may be naturally increased relative to other species of mRNA. That is, the term is meant to cover only those situations in which a person has intervened to elevate the proportion of the desired nucleic acid.

It is also advantageous for some purposes that a nucleotide sequence be in purified form. The term "purified" in reference to nucleic acid does to require absolute purity such as a homogeneous preparation); instead, it represents an indication that the sequence is relatively purer than in the natural environment (compared to the natural level this level should be at least 2–5 fold greater, e.g., in terms of mg/mL). Individual clones isolated from a cDNA library may be purified to electrophoretic homogeneity. The claimed DNA molecules obtained from these clones could be obtained directly from total DNA or from total RNA. The cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process which includes the construction of a cDNA library from mRNA and isolation of distinct cDNA clones yields an approximately $10^6$-fold purification of the native message. Thus purification of at least one order of magnitude, preferably two or three orders, and more preferably four or five orders of magnitude is expressly contemplated. The term is also chosen to distinguish clones already in existence which may encode ALK-7 but which have not been isolated from other clones in a library of clones. Thus, the term covers clones encoding ALK-7 which are isolated from other non-ALK-7 clones.

The term "nucleic acid molecule" describes a polymer of deoxyribonucleotides (DNA) or ribonucleotides (RNA). The nucleic acid molecule may be isolated from a natural source by cDNA cloning or subtractive hybridization or synthesized manually. The nucleic acid molecule may be synthesized manually by the triester synthetic method or by using an automated DNA synthesizer.

The term "cDNA cloning" refers to hybridizing a small nucleic acid molecule, a probe, to genomic cDNA. The probe hybridizes (binds) to complementary sequences of cDNA.

The term "complementary" describes two nucleotides that can form multiple favorable interactions with one another. For example, adenine is complementary to thymine as they can form two hydrogen bonds. Similarly, guanine and cytosine are complementary since they can form three hydrogen bonds. Thus if a nucleic acid sequence contains the following sequence of bases, thymine, adenine, guanine and cytosine, a "complement" of this nucleic acid molecule would be a molecule containing adenine in the place of thymine, thymine in the place of adenine, cytosine in the place of guanine, and guanine in the place of cytosine. Because the complement can contain a nucleic acid sequence that forms optimal interactions with the parent nucleic acid molecule, such a complement can bind with high affinity to its parent molecule.

The term "hybridize" refers to a method of interacting a nucleic acid sequence with a DNA or RNA molecule in solution or on a solid support, such as cellulose or nitrocellulose. If a nucleic acid sequence binds to the DNA or RNA molecule with high affinity, it is said to "hybridize" to the DNA or RNA molecule. The strength of the interaction between the probing sequence and its target can be assessed by varying the stringency of the hybridization conditions. Under highly stringent hybridization conditions only highly complementary nucleic acid sequences hybridize. Preferably, such conditions prevent hybridization of nucleic acids having one or two mismatches out of 20 contiguous nucleotides.

Various low or high stringency hybridization conditions may be used depending upon the specificity and selectivity desired. Stringency is controlled by varying salt or denaturant concentrations. Examples of hybridization conditions are shown in the examples below. High stringent conditions may mean conditions that are at least as stringent as the following: hybridization in 50% formamide, 5×SSC, 50 mM $NaH_3PO_4$, pH 6.8, 0.5% SDS, 0.1 mg/mL sonicated salmon sperm DNA, and 5×Denhart solution at 42° C. overnight; washing with 2×SSC, 0.1% SDS at 45° C.; and washing with 0.2×SSC, 0.1% SDS at 45° C. Those skilled in the art will recognize how such conditions can be varied to vary specificity and selectivity.

An ALK-7 polypeptide can be encoded by a full-length nucleic acid sequence or any portion of the full-length nucleic acid sequence. In preferred embodiments the isolated nucleic acid comprises, consists essentially of, or consists of a nucleic acid sequence set forth in SEQ ID NO:1, a nucleic acid sequence that hybridizes to the nucleic acid sequence set forth in SEQ ID NO:1 or a functional derivative (as defined below) of either of the foregoing. The nucleic acid may be isolated from a natural source by cDNA cloning or subtractive hybridization; the natural source may be mammalian (human) blood, semen, or tissue and the nucleic acid may be synthesized by the triester or other method or by using an automated DNA synthesizer.

The term "mammalian" refers to such organisms as mice, rats, rabbits, goats, more preferably monkeys and apes, and most preferably humans.

In other preferred embodiments, the nucleic acid molecule of the invention comprises a nucleotide sequence that (a) encodes a polypeptide having the full length amino acid sequence set forth in SEQ ID NO:2; (b) is the complement of the nucleotide sequence of (a); (c) hybridizes under highly stringent conditions to the nucleotide molecule of (a) and encodes a naturally occurring ALK-7 polypeptide; (d) encodes an ALK-7 polypeptide having the full length amino acid sequence of the sequence set forth in SEQ ID NO:2, except that it lacks one or more of the following segments of amino acid residues: 1–25, 26–113, 114–493, 137–493, 193–483 of SEQ ID NO:2; (e) is the complement of the nucleotide sequence of (d); (f) encodes a polypeptide having the amino acid sequence set forth in SEQ ID NO:2 from amino acid residues 1–25, 26–113, 114–493, 137–493, 193–483 of SEQ ID NO:2; (g) is the complement of the nucleotide sequence of (f); (h) encodes a polypeptide having the full length amino acid sequence set forth in SEQ ID NO:2, except that it lacks one or more of the domains selected from the group consisting of a signal peptide, an extracellular region, a transmembrane domain, a cytoplasmic domain, and a catalytic domain; or (i) is the complement of the nucleotide sequence of (h). The nucleic acid molecule of the invention is isolated, enriched, or purified from, preferably, a mammal, or most preferably from a human.

In yet other preferred embodiments the nucleic acid is an isolated conserved or unique region, for example those useful for the design of hybridization probes to facilitate identification and cloning of additional polypeptides, or for the design of PCR probes to facilitate cloning of additional polypeptides.

By "conserved nucleic acid regions," are meant regions present on two or more nucleic acids encoding an ALK-7 polypeptide, to which a particular nucleic acid sequence can hybridize under lower stringency conditions. Examples of lower stringency conditions suitable for screening for nucleic acid encoding ALK-7 polypeptides are provided in Abe, et al. *J. Biol. Chem.* 19:13361 (1992) (hereby incorporated by reference herein in its entirety, including and drawings). Preferably, conserved regions differ by no more than 5 out of 20 contiguous nucleotides.

By "unique nucleic acid region" is meant a sequence present in a full length nucleic acid coding for an ALK-7 polypeptides that is not present in a sequence condign for any other known naturally occurring polypeptide. Such regions preferably comprise 14, 17, 21 or more contiguous nucleotides present in the full length nucleic acid encoding an ALK-7 polypeptide. In particular, a unique nucleic acid region is preferably of human origin.

In yet another aspect, the invention relates to a nucleic acid vector comprising a nucleic acid molecule encoding an ALK-7 polypeptide and a promoter element effective to initiate transcription in a host cell.

The term "nucleic acid vector" relates to a single or double stranded circular nucleic acid molecule that can be transfected or transformed into cells and replicate independently or within the host cell genome. A circular double stranded nucleic acid molecule can be cut and thereby linearized upon treatment with restriction enzymes. An assortment of vectors, restriction enzymes, and the knowledge of the nucleotide sequences that the restriction enzymes operate upon are readily available to those skilled in the art. A nucleic acid molecule of the invention can be inserted into a vector by cutting the vector with restriction enzymes and ligating the two pieces together.

Many techniques are available to those skilled in the art to facilitate transformation or transfection of the expression construct into a prokaryotic or eukaryotic organism. The terms "transformation" and "transfection" refer to methods of inserting an expression construct into a cellular organism. These methods involve a variety of techniques, such as treating the cells with high concentrations of salt, an electric field, or detergent, to render the host cell outer membrane or wall permeable to nucleic acid molecules of interest.

The term "promoter element" describes a nucleotide sequence that is incorporated into a vector that, once inside an appropriate cell, can facilitate transcription factor and/or polymerase binding and subsequent transcription of portions of the vector DNA into mRNA. The promoter element precedes the 5' end of the ALK-7 nucleic acid molecule such that the latter is transcribed into mRNA. Host cell machinery then translates mRNA into a polypeptide.

Those skilled in the art would recognize that a nucleic acid vector can contain many other nucleic acid elements besides the promoter element and the ALK-7 nucleic acid molecule. These other nucleic acid elements include, but are not limited to, origins of replication, ribosomal binding sites, nucleic acid sequences encoding drug resistance enzymes or amino acid metabolic enzymes, and nucleic acid sequences encoding secretion signals, periplasm or peroxisome localization signals, or signals useful for polypeptide purification.

The invention also features a nucleic acid probe for the detection of a nucleic acid encoding a ALK-7 polypeptide in a sample.

The term "nucleic acid probe" refers to a nucleic molecule that is complementary to and can bind a nucleic acid sequence encoding the amino acid sequence substantially similar to that set forth in SEQ ID NO:2.

In preferred embodiments the nucleic acid probe hybridizes the nucleic acid encoding at least 14 contiguous amino acids of the full-length sequence set forth in SEQ ID NO:2 or a functional derivative thereof. Various low or high stringency hybridization conditions may be used depending upon the specificity and selectivity desired. Under highly stringent hybridization conditions only highly complementary nucleic acid sequences hybridize. Preferably, such conditions prevent hybridization of nucleic acids having 1 or 2 mismatches out of 20 contiguous nucleotides.

Methods of using the probes include detecting the presence or amount of ALK-7 RNA in a sample by contacting the sample with a nucleic acid probe under conditions such that hybridization occurs and detecting the presence or amount of the probe bound to ALK-7 RNA. The nucleic acid duplex formed between the probe and a nucleic acid sequence coding for an ALK-7 polypeptide may be used in the identification of the sequence of the nucleic acid detected (for example see, Nelson et al., in Nonisotopic DNA Probe Techniques, p. 275 Academic Press, San Diego (Kricka, et al., 1992) hereby incorporated by reference herein in its entirety, including any drawings). Kits for performing such methods may be constructed to include a container means having disposed therein a nucleic acid probe.

Another feature of the invention is a nucleic acid molecule as set forth in SEQ ID NO:1 or fragments thereof, comprising one or more regions that encode an ALK-7 polypeptide or an ALK-7 domain polypeptide, where the ALK-7 polypeptide or the ALK-7 domain polypeptide is fused to a non-ALK-7 polypeptide. Such fused polypeptides include, for example, but are not limited to, a GST-fusion protein.

The invention also features recombinant nucleic acid, preferably in a cell or an organism. The recombinant nucleic acid may contain a sequence set forth in SEQ ID NO:1 or a functional derivative thereof and a vector or a promoter effective to initiate transcription in a host cell. The recombinant nucleic acid can alternatively contain a transcriptional initiation region functional in a cell, a sequence complimentary to an RNA sequence encoding an ALK-7 polypeptide and a transcriptional termination region functional in a cell.

Another aspect of the invention relates to a recombinant cell or tissue comprising a nucleic acid molecule encoding an ALK-7 polypeptide. The recombinant cell may comprise a nucleic acid molecule encoding either an ALK-7 polypeptide; an ALK-7 domain polypeptide; or an ALK-7 polypeptide or ALK-7 domain polypeptide fused to a non-ALK-7 polypeptide.

The term "recombinant organism" refers to an organism that has a new combination of genes or nucleic acid molecules. A new combination of genes or nucleic acid molecules can be introduced to an organism using a wide array of nucleic acid manipulation techniques available to those skilled in the art.

The term "organism" relates to any living being comprised of a least one cell. An organism can be as simple as one eukaryotic cell or as complex as a mammal. Therefore, a recombinant organism can also be a recombinant cell, which may be a eukaryotic or a prokaryotic organism.

The term "eukaryote" refers to an organism comprised of cells that contain a nucleus. Eukaryotes are differentiated from "prokaryotes" which do not have a nucleus and lack other cellular structures found in eukaryotes, such as mitochondria and endoplasmic reticulum. Prokaryotes include unicellular organisms, such as bacteria, while eukaryotes are represented by yeast, invertebrates, and vertebrates.

The recombinant cell can harbor a nucleic acid vector that is extragenomic. The term "extragenomic" refers to a nucleic acid vector which does not insert into the cell genome. Many nucleic acid vectors are designed with their own origins of replication allowing them to utilize the recombinant cell replication machinery to copy and propagate the vector nucleic acid sequence. These vectors are small enough that they are not likely to harbor nucleic acid sequences homologous to genomic sequences of the recombinant cell. Thus these vectors replicate independently of the host genome and do not recombine with or integrate into the genome.

A recombinant cell can harbor a portion of a nucleic acid vector in an intragenomic fashion. The term "intragenomic" defines a nucleic acid construct that is incorporated within the cell genome. Multiple nucleic acid vectors available to those skilled in the art contain nucleic acid sequences that are homologous to nucleic acid sequences in a particular organism's genomic DNA. These homologous sequences will result in recombination events that integrate portions of the vector into the genomic DNA. Those skilled in the art can control which nucleic acid sequences of the vector are integrated into the cell genome by flanking the portion to be incorporated into the genome with homologous sequences in the vector.

Another aspect of the invention features an isolated, enriched, or purified ALK-7 polypeptide.

By "ALK-7 polypeptide" it is meant an amino acid sequence substantially similar to the sequence shown in SEQ ID NO:2, or fragments thereof. A sequence that is substantially similar will preferably have at least 90% identity (more preferably at least 95% and most preferably 99–100%) to the sequence of SEQ ID NO:2.

The ALK-7 polypeptides of the present invention preferably have a substantially similar biological activity to the protein encoded by the full length nucleic acid sequence set forth in SEQ ID NO:1 or to the proteins with amino acid sequence set forth in SEQ ID NO:2. By "biological activity" it is meant an activity of the ALK-7 protein in a cell. The biological activity of the ALK-7 is related to some of the activities of the cell which include, but are not limited to, cell proliferation motogenesis, metastasis, tumor escape, cell adhesion, transformation, or apoptosis.

By "identity" is meant a property of sequences that measures their similarity or relationship. Identity is measured by dividing the number of identical residues by the total number of residues and multiplying the product by 100. Thus, two copies of exactly the same sequence have 100% identity, but sequences that are less highly conserved and have deletions, additions, or replacements have a lower degree of identity. Those skilled in the art will recognize that several computer programs are available for determining sequence identity.

By "isolated" in reference to a polypeptide is meant a polymer of 6, 12, 18 or more amino acids conjugated to each other, including polypeptides that are isolated from a natural source or that are synthesized. The isolated polypeptides of the present invention are unique in the sense that they are not found in a pure or separated state in nature. Use of the term "isolated" indicates that a naturally occurring sequence has been removed from its normal cellular environment. Thus, the sequence may be in a cell-free solution or placed in a different cellular environment. The term does not imply that the sequence is the only amino acid chain present, but that it is essentially free (about 90–95% pure at least) of material naturally associated with it.

By the use of the term "enriched" in reference to a polypeptide it is meant that the specific amino acid sequence constitutes a significantly higher fraction (2–5 fold) of the total of amino acid sequences present in the cells or solution of interest than in normal or diseased cells or in the cells from which the sequence was taken. This could be caused by a person by preferential reduction in the amount of other amino acid sequences present, or by a preferential increase in the amount of the specific amino acid sequence of interest, or by a combination of the two. However, it should be noted that "enriched" does not imply that there are no other amino acid sequences present, just that the relative amount of the sequence of interest has been significantly increased.

The term "significant" here is used to indicate that the level of increase is useful to the person making such an increase, and generally means an increase relative to other amino acid sequences of about at least 2 fold, more preferably at least 5 to 10 fold or even more. The term also does not imply that there is no amino acid sequence from other sources. The other source amino acid sequence may, for example, comprise amino acid sequences encoded by a yeast or bacterial genome, or a cloning vector such as pUC19. The term is meant to cover only those situations in which a person has intervened to elevate the proportion of the desired nucleic acid.

It is also advantageous for some purposes that an amino acid sequence be in purified form. The term "purified" in reference to a polypeptide does not require absolute purity (such as a homogeneous preparation); instead it represents an indication that the sequence is relatively purer than in the natural environment (compared to the natural level this level should be at least 2–5 fold greater, e.g., in terms of mg/mL). Purification of at least one order of magnitude, preferably two or three orders of magnitude, and more preferably four or five orders of magnitude is expressly contemplated. The substance is preferably free of contamination at a functionally significant level, for example 90%, 95%, or 99% pure.

In another aspect the invention features an isolated, enriched, or purified ALK-7 polypeptide fragment.

By "an ALK-7 polypeptide fragment" it is meant an amino acid sequence that is less than the full-length ALK-7 amino acid sequence shown in SEQ ID NO:2. Examples of fragments include ALK-7 domains, ALK-7 mutants, and ALK-7 specific epitopes.

By "an ALK-7 domain" it is meant a portion of an ALK-7 polypeptide having homology to amino acid sequences from one or more known proteins wherein the sequence predicts some common function, interaction or activity. Well known examples of domains are the SH2 (SRC Homology 2) domain (Sadowski, et al., *Mol. Cell. Biol.* 6:4396, 1986; Pawson and Schlessinger, *Curr. Biol.* 3:434, 1993), the SH3 domain (Mayer, et al., *Nature* 332:272, 1988; Pawson and Schlessinger, *Curr. Biol.* 3:434, 1993), and Pleckstrin (PH) domain (Ponting, *TIBS* 21:245, 1996; Haslam, et al., *Nature* 363:309, 1993), all of which are domains that mediate protein:protein interaction, and the kinase catalytic domain (Hanks and Hunter, FASEB J 9:576–595, 1995). Computer programs designed to detect such homologies are well known in the art. The relative homology is at least 20%, more preferably at least 30% and most preferably at least 35%. Also within the scope of this definition are the extracellular domain, the signal sequence, the transmembrane domain, the juxtamembrane domain, the intracellular domain and the catalytic domain of an ALK-7 polypeptide, which are specific discernable portions of the protein.

By an "ALK-7 mutant" it is meant an ALK-7 polypeptide which differs from the native sequence in that one or more amino acids have been changed, added, or deleted. Changes in amino acids may be conservative or non-conservative. A "conservative" change means an amino acid is substituted with another amino acid with similar properties such as charge, hydrophobicity, structure, etc. Examples of polypeptides encompassed by this term include, but are not limited to (1) chimeric proteins which comprise a portion of an ALK-7 polypeptide sequence fused to a non-ALK-7 polypeptide sequence, for example a polypeptide sequence of the epidermal growth factor receptor, (2) ALK-7 proteins lacking a specific domain, for example the catalytic domain, and (3) ALK-7 proteins having a point mutation. An ALK-7 mutant will retain some useful function, such as ligand binding, catalytic activity, or the ability to bind to an ALK-7 specific antibody (as defined below).

By "ALK-7-specific epitope" it is meant a sequence of amino acids that is both antigenic and unique to ALK-7. ALK-7-specific epitope can be used to produce ALK-7-specific antibodies, as more fully described below. A particularly preferred epitope is amino acids 143 to 156 of SEQ ID NO:2.

By "recombinant ALK-7 polypeptide" it is meant to include a polypeptide produced by recombinant DNA techniques such that it is distinct from a naturally occurring polypeptide either in its location (e.g., present in a different cell or tissue than found in nature), purity, or structure. Generally, such a recombinant polypeptide will be present in a cell in an amount different from that normally observed in nature.

The polypeptide of the invention comprises an amino acid sequence having (a) the full length amino acid sequence set forth in SEQ ID NO:2; (b) the full length amino acid sequence of the sequence set forth in SEQ ID NO:2, except that it lacks one or more of the following segments of amino acid residues: 1–25, 26–113, 114–493, 137–493, 193–483 of SEQ ID NO:2; (c) the amino acid sequence set forth in SEQ ID NO:2 from amino acid residues 1–25, 26–113, 114–493, 137–493, 193–483 of SEQ ID NO:2; or (d) the full length amino acid sequence set forth in SEQ ID NO:2 except that it lacks one or more of the domains selected from the group consisting of a signal peptide, an extracellular region, a transmembrane domain, a cytoplasmic domain, and a catalytic domain.

In yet another aspect the invention features an antibody (e.g., a monoclonal or polyclonal antibody) having specific binding affinity to an ALK-7 polypeptide or ALK-7 polypeptide fragment. By "specific binding affinity" is meant that the antibody binds to target (ALK-7) polypeptides with greater affinity than it binds to other polypeptides under specified conditions. Antibodies having specific binding affinity to an ALK-7 polypeptide may be used in methods for detecting the presence and/or amount of an ALK-7 polypeptide in a sample by contacting the sample with the antibody under conditions such that an immunocomplex forms and detecting the presence and/or amount of the antibody conjugated to the ALK-7 polypeptide. Diagnostic kits for performing such methods may be constructed to include a first container containing the antibody and a second container having a conjugate of a binding partner of the antibody and a label, such as, for example, a radioisotope. The diagnostic kit may also include notification of an FDA approved use and instructions therefor.

The term "polyclonal" refers to antibodies that are heterogeneous populations of antibody molecules derived from the sera of animals immunized with an antigen or an antigenic functional derivative thereof. For the production of polyclonal antibodies, various host animals may be immunized by injection with the antigen. Various adjuvants may be used to increase the immunological response, depending on the host species.

"Monoclonal antibodies" are substantially homogenous populations of antibodies to a particular antigen. They may be obtained by any technique which provides for the production of antibody molecules by continuous cell lines in culture. Monoclonal antibodies may be obtained by methods known to those skilled in the art. See, for example, Kohler, et al., Nature 256:495–497 (1975), and U.S. Pat. No. 4,376,110.

The term "antibody fragment" refers to a portion of an antibody, often the hypervariable region and portions of the surrounding heavy and light chains, that displays specific binding affinity for a particular molecule. A hypervariable region is a portion of an antibody that physically binds to the polypeptide target.

In another aspect the invention features a hybridoma which produces an antibody having specific binding affinity to an ALK-7 polypeptide. By "hybridoma" is meant an immortalized cell line which is capable of secreting an antibody, for example an ALK-7 antibody. In preferred embodiments an ALK-7 antibody comprises a sequence of amino acids that is able to specifically bind an ALK-7 polypeptide.

The invention features a method for identifying human cells containing an ALK-7 polypeptide or a related sequence. The method involves identifying the novel polypeptide in human cells using techniques that are routine and standard in the art, such as those described herein for identifying ALK-7 (e.g., cloning, Southern or Northern blot analysis, in situ hybridization, PCR amplification, etc.).

The invention also features methods of screening cells for natural binding partners of ALK-7 polypeptides. By "natural binding partner" it is meant a protein that interacts with ALK-7. Binding partners include ligands, agonists, antagonists, and downstream signaling molecules, such as adaptor proteins, and may be identified by techniques well known in the art such as co-immunoprecipitation or by using, for example, a two-hybrid screen. (Fields and Song, U.S. Pat. No. 5,283,173, issued Feb. 1, 1994 and, incorporated by reference herein.) The present invention also features the purified, isolated or enriched versions of the polypeptides identified by the methods described above.

In another aspect, the invention provides a method for identifying a substance capable of modulating ALK-7 activity comprising the steps of (a) contacting an ALK-7 polypeptide with a test substance; and (b) determining whether the substance alters the activity of said polypeptide.

The invention also features another method of identifying substances capable of modulating the function of an ALK-7 polypeptide. The method comprises the following steps: (a) expressing an ALK-7 polypeptide in cells; (b) adding a compound to the cells; and (c) monitoring a change or an absence of a change in cell phenotype, cell proliferation, catalytic activity of the ALK-7 polypeptide, and binding a natural binding partner.

The term "compound" includes small organic molecules including, but not limited to, oxindolinones, quinazolines, tyrphostins, quinoxalines, and those contained within extracts from natural sources. Examples of such compounds are included in section XII, below.

The term "function" refers to the cellular role of a serine-threonine protein kinase. The serine-threonine protein kinase family includes members that regulate many steps in signaling cascades, including cascades controlling cell growth, migration, differentiation, gene expression, muscle contraction, glucose metabolism, cellular protein synthesis, and regulation of the cell cycle.

The term "modulates" refers to the ability of a compound to alter the function of a protein kinase. A modulator preferably activates the catalytic activity of a protein kinase, more preferably activates or inhibits the catalytic activity of a protein kinase depending on the concentration of the compound exposed to the protein kinase, or most preferably inhibits the catalytic activity of a protein kinase.

The term "catalytic activity," in the context of the invention, defines the ability of a protein kinase to phosphorylate a substrate. Catalytic activity can be measured, for example, by determining the amount of a substrate converted to a product as a function of time. Phosphorylation of a substrate occurs at the active-site of a protein kinase. The active-site is normally a cavity in which the substrate.

The term "substrate" as used herein refers to a molecule that is phoshorylated by or directly interacts with the protein kinase. The substrate is preferably a peptide and more preferably a protein. In relation to the protein kinase RAF, preferred substrates are MEK and the MEK substrate MAPK.

The term "activates" refers to increasing the cellular function of a protein kinase. The protein kinase function is preferably the interaction with a natural binding partner or catalytic activity.

The term "inhibit" refers to decreasing the cellular function of a protein kinase. The protein kinase function is preferably the interaction with a natural binding partner or catalytic activity.

The term "modulates" also refers to altering the function of a protein kinase by increasing or decreasing the probability that a complex forms between a protein kinase and a natural binding partner. A modulator preferably increases the probability that such a complex forms between the protein kinase and the natural binding partner, more preferably increases or decreases the probability that a complex forms between the protein kinase and the natural binding partner depending on the concentration of the compound exposed to the protein kinase, and most preferably decreases the probability that a complex forms between the protein kinase and the natural binding partner.

The term "complex" refers to an assembly of at least two molecules bound to one another. Signal transduction complexes often contain at least two protein molecules bound to one another, either transiently or in succession. For instance, a receptor protein tyrosine kinase, GRB2, SOS, and RAF sequentially interact in response to a mitogenic ligand.

The term "expressing" as used herein refers to the production of an ALK-7 polypeptide from a nucleic acid vector containing an ALK-7 gene within a cell. The nucleic acid vector is transfected into cells using well known techniques in the art as described herein.

The term "adding" as used herein refers to administering a solution comprising a compound to the medium bathing cells. The solution comprising the compound can also comprise an agent, such as dimethyl sulfoxide, which facilitates the uptake of the compound into the cells.

The term "monitoring" refers to observing the effect of adding the compound to the cells of the method. The effect can be manifested in a change in cell phenotype, cell proliferation, protein kinase catalytic activity, or in the interaction between a protein kinase and a natural binding partner.

The term "cell phenotype" refers to the outward appearance of a cell or tissue or the function of the cell or tissue. Examples of cell or tissue phenotype are cell size (reduction or enlargement), cell proliferation (increased or decreased numbers of cells), cell differentiation (a change or absence of a change in cell shape), cell survival, apoptosis (cell death), or the utilization of a metabolic nutrient (e.g., glucose uptake). Change or the absence of change in cell phenotype is readily measured by techniques known in the art.

The term "cell proliferation" refers to the rate at which a group of cells divides. The number of cells growing in a vessel can be quantitated by a person skilled in the art when that person visually counts the number of cells in a defined area using a common light microscope. Alternatively, cell proliferation rates can be quantitated by laboratory apparatae that optically measure the density of cells in an appropriate medium.

The method can utilize any of the molecules disclosed in the invention. These molecules include nucleic acid molecules encoding ALK-7 polypeptides, nucleic acid vectors, recombinant cells, polypeptides, or antibodies of the invention.

In a preferred embodiment, the invention provides a method for treating or preventing an abnormal condition by administering a compound which is a modular of ALK-7 function in vitro. The abnormal condition preferably involves abnormality in ALK-7 signal transduction pathway, and most preferably is cancer. Such compounds preferably show positive results in one or more in vitro assays for an activity corresponding to treatment of the disease or disorder in question (such as the assays described in Example 5 below). Examples of substances that can be screened for favorable activity are provided in section XII below.

The summary of the invention described above is non-limiting and other features and advantages of the invention will be apparent from the following detailed description, and from the claims.

DETAILED DESCRIPTION OF THE INVENTION

The present invention relates to the isolation and characterization of a new protein which we have called ALK-7, nucleotide sequences encoding ALK-7, various products and assay methods that can be used to identify compounds useful for the diagnosis and treatment of various ALK-7 related diseases and conditions, for example neurological disorders. Polypeptides derived from ALK-7 and nucleic acids encoding such polypeptides may be produced using well known standard synthesis techniques when given the sequence presented herein.

ALK-7 is a type I receptor serine/threonine kinase (STK receptor). Proteins with some homology have been described in the rat (Ryde, et al., *J. Biol. Chem.* 271:30603, 1996; Tsuchida, et al., *Molec. Cell. Neurosci.* 7:467, 1996), however, unlike the rat proteins, the human ALK-7 is expressed in more restricted regions of the brain, notably hippocampus, hypothalamic nuclei, substantia nigra and pituitary. This extremely restricted expression pattern strongly suggests a role for human ALK-7 in the growth and/or survival of neurons and its relevance in treatment of such diseases as Parkinson's disease, Huntington's disease and Alzheimer's disease.

The polypeptide and nucleotide sequences of the invention can be used, therefore, to identify modulators of cell growth and survival which are useful in developing therapeutics for various neurological diseases and conditions. For example, an ALK-7 polypeptide can be used to identify ligands that can be used as biopharmaceuticals to promote the growth and survival of neurons. Promotion of growth and survival may be accomplished directly by stimulating mitogenesis and/or differentiation of cells or by modulation of neurotransmitter activity. Assays to identify compounds that act intracellularly to enhance or inhibit ALK-7 activity can be developed by creating genetically engineered cell lines that express ALK-7 nucleotide sequences, as is more fully discussed below.

I. Nucleic Acids Encoding ALK-7 Polypeptides

A first aspect of the invention features nucleic acid sequences encoding an ALK-7 polypeptide. Included within the scope of this invention are the functional equivalents of the herein-described isolated nucleic acid molecules. Functional equivalents or derivatives can be obtained in several ways. The degeneracy of the genetic code permits substitution of certain codons by other codons which specify the same amino acid and hence would give rise to the same protein. The nucleic acid sequence can vary substantially since, with the exception of methionine and tryptophan, the known amino acids can be coded for by more than one codon. Thus, portions or all of an ALK-7 gene could be synthesized to give a nucleic acid sequence significantly different from that shown in SEQ ID NO:1. The encoded amino acid sequence thereof would, however, be preserved.

In addition, the nucleic acid sequence may comprise a nucleotide sequence which results from the addition, deletion or substitution of at least one nucleotide to the 5'-end and/or the 3'-end of the nucleic acid formula shown in SEQ ID NO:1 or a derivative thereof. Any nucleotide or polynucleotide may be used in this regard, provided that its addition, deletion or substitution does not alter the amino acid sequence of SEQ ID NO:2 which is encoded by the nucleotide sequence. For example, the present invention is intended to include any nucleic acid sequence resulting from the addition of ATG as an initiation codon at the 5'-end of an ALK-7 nucleic acid sequence or its functional derivative, or from the addition of TTA, TAG or TGA as a termination codon at the 3'-end of the inventive nucleotide sequence or its derivative. Moreover, the nucleic acid molecule of the present invention may, as necessary, have restriction endonuclease recognition sites added to its 5'-end and/or 3'-end.

Such functional alterations of a given nucleic acid sequence afford an opportunity to promote secretion and/or processing of heterologous proteins encoded by foreign nucleic acid sequences fused thereto. All variations of the nucleotide sequence of the ALK-7 genes and fragments thereof permitted by the genetic code are, therefore, included in this invention.

Further, it is possible to delete codons or to substitute one or more codons by codons other than degenerate codons to produce a structurally modified polypeptide, but one which has substantially the same utility or activity of the polypeptide produced by the unmodified nucleic acid molecule. As recognized in the art, the two polypeptides are functionally equivalent, as are the two nucleic acid molecules which give rise to their production, even though the differences between the nucleic acid molecules are not related to degeneracy of the genetic code.

Functional equivalents or derivatives of ALK-7 can also be obtained using nucleic acid molecules encoding one or more functional domains of an ALK-7 polypeptide. For example, the extracellular domain of ALK-7 functions as a ligand or co-receptor binding domain and a nucleic acid sequence encoding the extracellular domain alone or linked to other heterologous nucleic acid sequences can be considered a functional derivative of ALK-7. Other functional domains of ALK-7 include, but are not limited to, the signal sequence, the transmembrane domain, the intracellular domain and the catalytic domain. Nucleic acid sequences encoding these domains are shown in SEQ ID NO:1 as follows: signal sequence 155–229; extracellular domain 155–493; transmembrane domain 494–568; intracellular domain 569–1633; catalytic domain approximately 731–1609. It should be noted that the signal sequence is cleaved from the extracellular domain in the mature protein.

II. A Nucleic Acid Probe for the Detection of ALK-7

A nucleic acid probe of the present invention may be used to probe an appropriate chromosomal or cDNA library by usual hybridization methods to obtain another nucleic acid molecule of the present invention. A chromosomal DNA or cDNA library may be prepared from appropriate cells according to recognized methods in the art (e.g. "Molecular Cloning: A Laboratory Manual," second edition, edited by Sambrook Fritsch, & Maniatis, Cold Spring Harbor Laboratory, 1989).

In the alternative, chemical synthesis is carried out in order to obtain nucleic acid probes having nucleotide sequences which correspond to N-terminal and C-terminal portions of the amino acid sequence of the polypeptide of interest. Thus, the synthesized nucleic acid probes may be used as primers in a polymerase chain reaction (PCR) carried out in accordance with recognized PCR techniques, essentially according to PCR Protocols, "A Guide to Methods and Applications," edited by Michael et al., Academic Press, 1990, utilizing the appropriate chromosomal or cDNA library to obtain the fragment of the present invention.

One skilled in the art can readily design such probes based on the sequence disclosed herein using methods of computer alignment and sequence analysis known in the art (e.g. "Molecular Cloning: A Laboratory Manual," second edition, edited by Sambrook, Fritsch, & Maniatis, Cold Spring Harbor Laboratory, 1989). The hybridization probes of the present invention can be labeled by standard labeling techniques such as with a radiolabel, enzyme label, fluorescent label, biotin-avidin label, chemiluminescence, and the like. After hybridization, the probes may be visualized using known methods.

The nucleic acid probes of the present invention include RNA as well as DNA probes and nucleic acids modifies in the sugar, phosphate or even the base proton as long as the probe still retains the ability to specifically hybridize under conditions as disclosed herein. Such probes are generated using techniques known in the art. The nucleic acid probe may be immobilized on a solid support. Examples of such solid supports include, but are not limited to, plastics such as polycarbonate, complex carbohydrates such as agarose and sepharose, acrylic resins, such a polyacrylamide and latex beads, and nitrocellulose. Techniques for coupling nucleic acid probes to such solid supports are well known in the art.

The test samples suitable for nucleic acid probing methods of the present invention include, for example, cells or nucleic acid extracts of cells, or biological fluids. The sample used in the above-described methods will vary based on the assay format, the detection method and the nature of the tissues, cells or extracts to be assayed. Methods for preparing nucleic acid extracts of cells are well known in the art and can be readily adapted in order to obtain a sample which is compatible with the method utilized.

III. A Probe Based Method and Kit for Detecting ALK-7

One method of detecting the presence of ALK-7 in a sample comprises (a) contacting said sample with the above-described nucleic acid probe, under conditions such that hybridization occurs, and (b) detecting the presence of said probe bound to said nucleic acid molecule. One skilled in the art would select the nucleic acid probe according to techniques known in the art as described above. Samples to be tested include but should not be limited to RNA samples of human tissue.

A kit for detecting the presence of ALK-7 in a sample comprises at least one container having disposed therein the above-described nucleic acid probe. The kit may further comprise other containers comprising one or more of the following: wash reagents and reagents capable of detecting the presence of bound nucleic acid probe. Examples of detection reagents include, but are not limited to radiolabelled probes, enzymatic labeled probes (horseradish peroxidase, alkaline phosphatase), and affinity labeled probes (biotin, avidin, or steptavidin).

In detail, a compartmentalized kit includes any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another. Such containers will include a container which will accept the test sample, a container which contains the probe or primers used in the assay, containers which contain wash reagents (such as phosphate buffered saline, Tris-buffers, and the like), and container which contain the reagents used to detect the hybridized probe, bound antibody, amplified product, or the like. One skilled in the art will readily recognize that the nucleic acid probes described in the present invention can readily be incorporated into one of the established kit formats which are well known in the art.

IV. DNA Constructs Comprising an ALK-7 Nucleic Acid Molecule and Cells Containing These Constructs The present invention also relates to a recombinant DNA molecule comprising, 5' to 3', a promoter effective to initiate transcription in a host cell and the above-described nucleic acid molecules. In addition, the present invention relates to a recombinant DNA molecules comprising a vector and a nucleic acid molecule described herein. The present invention also relates to a nucleic acid molecule comprising a transcriptional region functional in a cell, a sequence complimentary to an RNA sequence encoding an amino acid sequence corresponding to an ALK-7 polypeptide or functional derivative, and a transcriptional termination region functional in said cell. The above-described molecules may be isolated and/or purified DNA molecules.

The present invention also relates to a cell or organism that contains an ALK-7 nucleic acid molecule as described herein and thereby is capable of expressing a peptide. The polypeptide may be purified from cells which have been altered to express the polypeptide. A cell is said to be "altered to express a desired polypeptide" when the cell, through genetic manipulation, is made to produce a protein which it normally does not produce or which the cell normally provides at lower levels. One skilled in the art can readily adapt procedures for introducing and expressing either genomic, cDNA, or synthetic sequences into either eukaryotic or prokaryotic cells.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene sequence expression. The precise nature of the regulatory regions needed for gene sequence expression may vary from organism to organism, but will in general include a promoter region which, in prokaryotes, contains both the promoter (which directs the initiation of RNA transcription) as well as the DNA sequences which, when transcribed into RNA, will signal synthesis initiation. Such regions will normally include those 5'-non-coding sequences involved with initiation of transcription and translation, such as the TATA box, capping sequence, CAAT sequence, and the like.

If desired, the non-coding region 3' to the sequence encoding an ALK-7 gene may be obtained by the above-described cloning methods. This region may be retained for its transcriptional termination regulatory sequences, such as termination and polyadenylation. Thus, by retaining the 3'-region naturally contiguous to the DNA sequence encoding an ALK-7 gene, the transcriptional termination signal may be provided. Where the transcriptional termination signals are not satisfactorily functional in the expression host cell, then a 3' region functional in the host cell may be substituted.

Two DNA sequences (such as a promoter region sequence and an ALK-7 sequence) are said to be operably linked in the nature of the linkage between the two DNA sequences does no (1) result in the introduction of a frame-shift mutation, (2) interfere with the ability of the promoter region sequence to direct the transcription of an ALK-7 gene sequence, or (3) interfere with the ability of the an ALK-7 gene sequence to be transcribed by the promoter region sequence. Thus, a promoter region would be operably linked to a DNA sequence if the promoter were capable of effecting transcription of that DNA sequence. Thus, to express an ALK-7 gene, transcriptional and translational signals recognized by an appropriate host are necessary.

The present invention encompasses the expression of an ALK-7 gene (or a functional derivative thereof) in either prokaryotic or eukaryotic cells. Prokaryotic hosts are, generally, very efficient and convenient for the production of recombinant proteins and are, therefore, one type of preferred expression system for an ALK-7 gene. Prokaryotes most frequently are represented by various trans of *E. coli*. However, other microbial strains may also be used, including other bacterial strains.

In prokaryotic systems, plasmid vectors that contain replication sites and control sequences derived from a species compatible with the host may be used. Examples of suitable plasmid vectors may include pBR322, pUC118, pUC119 and the like; suitable phage or bacteriophage vectors may include λgt10, λgt11 and the like; and suitable virus vectors may include pMAM-neo, pKRC and the like. Preferably, the selected vector of the present invention has the capacity to replicate in the selected host cell.

Recognized prokaryotic hosts include bacteria such a *E. coli* and those from general such as Bacillus, Streptomyces, Pseudomonas, Salmonella, Serratia, and the like. However, under such conditions, the polypeptide will not be glycosylated. The prokaryotic host must be compatible with the replicon and control sequences in the expression plasmid.

To express ALK-7 (or a functional derivative thereof) in a prokaryotic cell, it is necessary to operably link an ALK-7 sequence to a functional prokaryotic promoter. Such promoters may be either constitutive or, more preferably, regulatable (i.e., inducible or derepressible). Examples of constitutive promoters include the the promoter of bacteriophage λ, the bla promoter of the β-lactamase gene sequence of pBR322, and the CAT promoter of the chloramphenicol acetyl transferase gene sequence of pPR325, and the like. Examples of inducible prokaryotic promoters include the major right and left promoter of bacteriophage λ ($P_L$ and $P_R$), the trp, recA, lacZ, lacI, and gal promoters of *E. coli*, the a-amylase (Ulmanen et al., *J. Bacteriol.* 162:176–182, 1985) and the sigma-28-specific promoters of *B. subtilis* (Gilman et al., *Gene sequence* 32:11–20(1984)), the promoters of the bacteriophages of Bacilllus (Gryczan, In: The Molecular Biology of the Bacilli, Academic Press, Inc., NY (1982)), and Streptomyces promoters (Ward et al., *Mol. Gen. Genet.* 203:468–478, 1986). Prokaryotic promoters are reviewed by Glick (*J. Ind. Microbiot.* 1:277–282, 1987); Cenatiempo (*Biochimie* 68:505–516, 1986); and Gottesman (*Ann. Rev. Genet.* 18:415–442, 1984).

Proper expression in a prokaryotic cell also requires the presence of a ribosome binding site upstream of the gene sequence-encoding sequence. Such ribosome binding sites are disclosed, for example, by Gold et al. (*Ann. Rev. Microbiol.* 35:365–404, 1981). The selection of control sequences, expression vectors, transformation methods, and the like, are dependent on the type of host cell used to express the gene.

As used herein, "cell," "cell line," and "cell culture" may be used interchangeably and all such designations include progeny. Thus, the words "transformants" or "transformed cells" include the primary subject cell and cultures derived therefrom, without regard to the number of transfers. It is also understood that all progeny may not be precisely identical in DNA content, due to deliberate or inadvertent mutations. However, as defined, mutant progeny have the same functionality as that of the originally transformed cell.

Host cells which may be used in the expression systems of the present invention are not strictly limited, provided that they are suitable for use in the expression of an ALK-7 peptide of interest. Suitable hosts may often include eukaryotic cells. Preferred eukaryotic hosts include, for example, yeast, fungi, insect cells, mammalian cells either in vivo, or in tissue culture. Mammalian cells which may be useful as hosts include HeLa cells, cells of fibroblast origin such as VERO, 3T3 or CHO-K1, or cells of lymphoid origin (such as 32D cells) and their derivatives. Preferred mammalian host cells include SP2/0 and J558L, as well as neuroblastoma cell lines such as IMR 332 and PC12 which may provide better capacities for correct post-translational processing.

In addition, plant cells are also available as hosts, and control sequences compatible with plant cells are available, such as the cauliflower mosaic virus 35S and 19S, and opaline synthase promoter and polyadenylation signal sequences. Another preferred host is an insect cell, for example the Drosophila larvae. Using insect cells as hosts, the Drosophila alcohol dehydrogenase promoter can be used. Rubin, *Science* 240:1453–1459, 1988). Alternatively baculovirus vectors can be engineered to express large amounts of ALK-7 in insects cells (Jasny, *Science* 238:1653, 1987); Miller et al., In: Genetic Engineering (1986), Setlow, J. K., et al., eds., Plenum, Vol. 8, pp. 277–297).

Any of a series of yeast gene sequence expression systems can be utilized which incorporate promoter and termination elements from the actively expressed gene sequences coding for glycolytic enzymes are produced in large quantities when years are grown in mediums rich in glucose. Known glycolytic gene sequences can also provide very efficient transcriptional control signals. Yeast provides substantial advantages in that it can also carry out post-translational peptide modifications. A number of recombinant DNA strategies exist which utilize strong promoter sequences and high copy number of plasmids which can be utilized for production of the desired proteins in yeast. Yeast recognizes leader sequences on cloned mammalian gene sequence products and secretes peptides bearing leader sequences (i.e., prepeptides). For a mammalian host, several possible vector systems are available for the expression of ALK-7.

A wide variety of transcriptional and translational regulatory sequences may be employed, depending upon the nature of the host. The transcriptional and translational regulatory signals may be derived from viral sources, such as adenovirus, bovine papilloma virus, cytomegalovirus, simian virus, or the like, where the regulatory signals are associated with a particular gene sequence which has a high level of expression. Alternatively, promoters from mammalian expression products, such as actin, collagen, myosin, and the like, may be employed. Transcriptional initiation regulatory signals may be selected which allow for repression or activation, so that expression of the gene sequences can be modulated. Of interest are regulatory signals which are temperature-sensitive so that by varying the temperature, expression can be repressed or initiated, or are subject to chemical (such as metabolite) regulation.

Expression of ALK-7 in eukaryotic hosts requires the use of eukaryotic regulatory regions. Such regions will, in general, include a promoter region sufficient to direct the initiation or RNA synthesis. Preferred eukaryotic promoters include, for example, the promoter of the mouse metallothionein I gene sequence (Hamer et al., *J. Mol. Appl. Gen.* 1:273–288, 1982); the TK promoter of Herpes virus (McKnight, *Cell* 31:355–365, 1982); the SV40 early promoter (Benoist et al., *Nature* (London) 290:304–310, 1981); the yeast ga14 gene sequence promoter (Johnston et al., *Proc. Natl. Acad. Sci.* (USA) 79:6971–6975, 1982); Silver et al., *Proc. Natl. Acad. Sci.* (USA) 81:5951–5955, 1984).

Translation of eukaryotic mRNA is initiated at the codon which encodes the first methionine. For this reason, it is preferable to ensure that the linkage between a eukaryotic promoter and a DNA sequence which encodes ALK-7 (or a functional derivative thereof) does not contain any intervening codons which are capable of encoding a methionine (i.e., AUG). The presence of such codons results either in a formation of a fusion protein (if the AUG codon is in the same reading frame as an ALK-7 coding sequence) or a frame-shift mutation (if the AUG codon is not in the same reading frame as an ALK-7 coding sequence).

An ALK-7 nucleic acid molecule and an operably linked promoter may be introduced into a recipient prokaryotic or eukaryotic cell either as a nonreplicating DNA (or RNA) molecule, which may either be a linear molecule or, more preferably, a closed covalent circular molecule (a plasmid). Since such molecules are incapable of autonomous replication, the expression of the gene may occur through the transient expression of the introduced sequence. Alternatively, permanent or stable expression may occur through the integration of the introduced DNA sequence into the host chromosome.

A vector may be employed which is capable of integrating the desired gene sequences into the host cell chromosome.

Cells which have stably integrated the introduced DNA into their chromosomes can be selected by also introducing one or more markers which allow for selection of host cells which contain the expression vector. The marker may provide for prototrophy to an auxotrophic host, biocide resistance, e.g., antibiotics, or heavy metals, such as copper, or the like. The selectable marker gene sequence can either be directly linked to the DNA gene sequences to be expressed, or introduced into the same cell by co-transfection. Additional elements may also be needed for optimal synthesis of single chain binding protein mRNA. These elements may include splice signals, as well as transcription promoters, enhancers, and termination signals. cDNA expression vectors incorporating such elements include those described by Okayama, *Molec. Cell. Bio.* 3:280(1983).

The introduced nucleic acid molecule can be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred prokaryotic vectors include plasmids such as those capable of replication in *E. coli* (such as, for example, pBR322, ColEl, pSC101, pACYC 184, pVX. Such plasmids are, for example, disclosed by Sambrook (cf. "Molecular Cloning: A Laboratory Manual," second edition, edited by Sambrook, Fritsch, & Maniatis, Cold Spring Harbor Laboratory, (1989)). Bacillus plasmids include pC194, pC221, pT127, and the like. Such plasmids are disclosed by Gryczan (In: The Molecular Biology of the Bacilli, Academic Press, NY (1982), pp. 307–329). Suitable Streptomyces plasmids include p1J101 (Kendall et al., *J. Bacteriol.* 169:4177–4183, 1987), and streptomyces bacteriophages such as fC31 (Chater et al., In: Sixth International Symposium on Actinomycetales Biology, Akademiai Kaido, Budapest, Hungary (1986), pp. 45–54). Pseudomonas plasmids are reviewed by John et al. (*Rev._Infect. Dis.* 8:693–704, 1986), and Izaki (*Jpn. J. Bacteriol.* 33:729–742, 1978).

Preferred eukaryotic plasmids include, for example, BPV, vaccinia, SV40, 2-micron circle, and the like, or their derivatives. Such plasmids are well known in the art (Botstein et al., Miami Wntr. Symp. 19:265–274, 1982); Broach, In: "The Molecular Biology of the Yeast Saccharomyces: Life Cycle and Inheritance," Cold Spring Harbor Laboratory, Cold Spring Harbor, N.Y., p. 445–470 (1981); Broach, *Cell* 28:203–204, 1982); Bollon et al., *J. Clin. Hematol. Oncol.* 10:39–48, 1980); Maniatis, In: Cell Biology: A Comprehensive Treatise, Vol. 3, Gene Sequence Expression, Academic Press, NY, pp. 563–608 (1980).

Once the vector or nucleic acid molecule containing the construct(s) has been prepared for expression, the DNA construct(s) may be introduced into an appropriate host cell by any of a variety of suitable means, i.e., transformation, transfection, conjugation, protoplast fusion, electroporation, particle gun technology, calcium phosphate-precipitation, direct microinjection, and the like. After the introduction of the vector, recipient cells are grown in a selective medium, which selects for the growth of vector-containing cells. Expression of the cloned gene molecule(s) results in the production of ALK-7 or fragments or functional derivatives thereof. This can take place in the transformed cells as such, or following the induction of these cells to differentiate (for example, by administration of bromodeoxyuracil to neuroblastoma cells or the like). A variety of incubation conditions can be used to form the peptide of the present invention. The most preferred conditions are those which mimic physiological conditions.

V. ALK-7 Polypeptides

Also a feature of the invention are ALK-7 polypeptides. A variety of methodologies known in the art can be utilized to obtain the polypeptides of the present invention. They may be purified from tissues or cells which naturally produce them. Alternatively, the above-described isolated nucleic acid sequences can be used to express an ALK-7 protein recombinantly.

Any eukaryotic organism can be used as a source for the polypeptide of the invention, as long as the source organism naturally contains such a polypeptide. As used herein, "source organism" refers to the original organism from which the amino acid sequence is derived, regardless of the organism protein is expressed in and ultimately isolated from.

One skilled in the art can readily follow known methods for isolating proteins in order to obtain the peptide free of natural contaminants. These include, but are not limited to: size-exclusion chromatography, HPLC, ion-exchange chromatography, and immuno-affinity chromatography.

An ALK-7 protein, like all proteins, is comprised of distinct functional units or domains. In eukaryotes, proteins sorted through the so-called vesicular pathway (bulk flow) usually have a signal sequence (also called a leader peptide) in the N-terminus, which is cleaved off after the translocation through the ER (endoplasmic reticulum) membrane. Some N-terminal signal sequences are not cleaved off, remaining as transmembrane segments, but it does not mean these proteins are retained in the ER; they can be further sorted and included in vesicles. Receptor proteins also have, and are somewhat defined by, a hydrophobic transmembrane segment(s) which are thought to be alpha-helices in membranes. Membrane proteins also integrate into the cell membrane in a specific manner with respect to the two sides (cytoplasmic/intracellular or exo-cytoplasmic/extracellular), which is referred to as membrane topology. Extracellular portions of integral membrane proteins often function a ligand binding domains whereas intracellular portions generally function to transmit signals within the cell, either by providing sites for protein:protein interactions or by having some catalytic activity (contained within a catalytic domain), often both. Methods of predicting the existence of these various domains are well known in the art. See, for example, D. J. McGeoch, *Virus Research* 3:271, 1985 or G. von Heijne, *Nucl. Acids Res.* 14:4683, 1986 for signal sequences, P. Klein, et al., *Biochim. Biophys. Acta* 815:468, 1985 for transmembrane domains and S. J. Singer, *Ann. Rev. Cell Biol.* 6:247, 1990 or E. Hartmann et al., *Proc. Natl. Acad. Sci. USA,* 86:5786, 1989 for prediction of membrane topology, all of which are incorporated by reference herein. Kinase catalytic domains can be identified by comparison to other known catalytic domains with kinase activity. See, for example Hanks and Hunter, *FASEB J.* 9:576–595, 1995.

Primary sequence analysis of an ALK-7 amino acid sequence (shown in SEQ ID NO:2) reveals that it contains all the motifs characteristic of a type I STK receptor. These include a 25 amino acid signal peptide (shown from amino acid number 1–25 of SEQ ID NO:2), and 88 amino acid cysteine-rich extracellular region (shown from amino acid number 26–113 of SEQ ID NO:2), a single 25 amino acid transmembrane domain (shown from amino acid number 114–136 of SEQ ID NO:2), and a 355 amino acid cytoplasmic domain (shown from amino acid number 137–493 of SEQ ID NO:2), which includes a GS domain and a catalytic domain (amino acid number 193–485 of SEQ ID NO:2).

The extracellular domain conserves the 10 cysteines present in all type I STK receptors (ten Dijke, et al., *Oncogene* 8:2879, 1993; Bassinge, et al., *Science* 263:87, 1994; Massague, *Trends Cell Biol.* 4:172, 1994) and also contains 3 potential N-linked glycosylation sites. The divergent extracellular domain sequence of ALK-7 (28–30% identity to ALK-4 and ALK-5) suggests it may have a unique ligand/type II STK receptor specificity. A rat ALK-7-like protein has been found to bind TGFbeta and activin in a complex with the type II TGFbeta receptor and ACTRII. However, these ligands are not expressed in the same cell types as human ALK-7 suggesting alternative ligands. Candidate ALK-7-specific ligands include other TGFbetas such as TGFbeta 2, GDF-1 and homologues of GDNF such a neuturin, which have been found to be expressed in neurons in a pattern similar to that of ALK-7.

The intracellular domain is somewhat more homologous to other ALK proteins, particularly in the catalytic domain which shows 83% identity to other type I STK receptors. The 40 amino acids immediately N-terminal of the transmembrane domain (the juxtamembrane domain) are, however, quite unique in comparison with other ALKs.

These ALK-7 domains have a variety of uses. An example of such a use is to make a polypeptide consisting of an ALK-7 extracellular domain and the transmembrane domain. Such a polypeptide, when expressed in a cell, is able to form heterotetrameric complexes with type II receptors but unable to transmit any signal further downstream into the cell, i.e. it would be signaling incompetent and thus would be useful for studying the biological relevance of ALK-7 activity. (See, for example, Millauer, et al., *Nature* 367:576, 1994.)

VI. An Antibody Having Binding Affinity to an ALK-7 Polypeptide and a Hybridoma Containing the Antibody The present invention also relates to an antibody having specific binding affinity to an ALK-7 polypeptide. The polypeptide may have the amino acid sequence set forth in SEQ ID NO:2, or a be fragment thereof, or at least 6 contiguous amino acids thereof. Such an antibody may be identified by comparing its binding affinity to a ALK-7 polypeptide with its binding affinity to another polypeptide. Those which bind selectively to ALK-7 would be chosen for use in methods requiring a distinction between ALK-7 and other polypeptides. Such methods could include, but should not be limited to, the analysis of altered ALK-7 expression in tissue containing other polypeptides and assay systems using whole cells.

An ALK-7 peptide of the present invention can be used to produce antibodies or hybridomas. One skilled in the art will recognize that if an antibody is desired, such a peptide would be generated as described herein and used as an immunogen. A preferred ALK-7 peptide in this respect is the sequence from amino acids 143 to 156 of SEQ ID NO:2. The antibodies of the present invention include monoclonal and polyclonal antibodies, as well fragments of these antibodies, and humanized forms. Humanized forms of the antibodies of the present invention may be generated using one of the procedures known in the art such as chimerization or CDR grafting. The present invention also relates to a hybridoma which produces the above-described monoclonal antibody, or binding fragment thereof. A hybridoma is an immortalized cell line which is capable of secreting a specific monoclonal antibody.

In general, techniques for preparing monoclonal antibodies and hybridomas are well known in the art (Campbell, "Monoclonal Antibody Technology: Laboratory Techniques in Biochemistry and Molecular Biology," Elsevier Science Publishers, Amsterdam, The Netherlands, 1984; St. Groth et al., *J. Immunol. Methods* 35:1–21, 1980). Any animal (mouse, rabbit, and the like) which is known to produce antibodies can be immunized with the selected polypeptide. Methods for immunization are well known in the art. Such methods include subcutaneous or intraperitoneal injection of the polypeptide. One skilled in the art will recognize that the amount of polypeptide used for immunization will vary based on the animal which is immunized, the antigenicity of the polypeptide and the site of injection.

The polypeptide may be modified or administered in an adjuvant in order to increase the peptide antigenicity. Methods of increasing the antigenicity of a polypeptide are well known in the art. Such procedures include coupling the antigen with a heterologous protein (such as globulin or β-galactosidase) or through the inclusion of an adjuvant during immunization.

For monoclonal antibodies, spleen cells from the immunized animals are removed, fused with myeloma cells, such as SP/0-Ag14 myeloma cells, and allowed to become monoclonal antibody producing hybridoma cells. Any one of a number of methods well known in the art can be used to identify the hybridoma cell which produces an antibody with the desired characteristics. These include screening the hybridomas with an ELISA assay, western blot analysis, or radioimmunoassay (Lutz, et al., *Exp. Cell Res.* 175:109–124, 1988). Hybridomas secreting the desired antibodies are cloned and the class and subclass is determined using procedures known in the art (Campbell, "Monoclonal Antibody Technology: Laboratory Techniques in Biochemistry and Molecular Biology," supra, 1984).

For polyclonal antibodies, antibody containing antisera is isolated from the immunized animal and is screened for the presence of antibodies with the desired specificity using one of the above-described procedures. The above-described antibodies may be detectably labeled. Antibodies can be detectably labeled through the use of radioisotopes, affinity labels (such as biotin, avidin, and the like), enzymatic labels (such as horse radish peroxidase, alkaline phosphatase, and the like) fluorescent labels (such as FITC or rhodamine, and the like), paramagnetic atoms, and the like. Procedures for accomplishing such labeling are well-known in the art, for example, see (Stemberger, et al., *J. Histochem. Cytochem.* 18:315, 1970; Bayer, et al., *Meth. Enzym.* 62:308, 1979; Engval, et al., *Immunot.* 109:129, 1972; Goding, *J. Immunol. Meth.* 13:215, 1976). The labeled antibodies of the present invention can be used for in vitro, in vivo, and in situ assays to identify cells or tissues which express a specific peptide.

The above-described antibodies may also be immobilized on a solid support. Examples of such solid supports include plastics such as polycarbonate, complex carbohydrates such as agarose and sepharose, acrylic resins and such a polyacrylamide and latex beads. Techniques for coupling antibodies to such solid supports are well known in the art (Weir et al., "Handbook of Experimental Immunology" 4th Ed., Blackwell Scientific Publications, Oxford, England, Chapter 10, 1986; Jacoby et al., Meth. Enzym. 34, Academic Press, N.Y., 1974). The immobilized antibodies of the present invention can be used for in vitro, in vivo, and in situ assays as well as in immunochromatography.

Furthermore, one skilled in the art can readily adapt currently available procedures, as well as the techniques, methods and kits disclosed above with regard to antibodies, to generate peptides capable of binding to a specific peptide sequence in order to generate rationally designed antipeptide peptides, for example see Hurby et al., "Application of Synthetic Peptides: Antisense Peptides," In Synthetic Peptides, A User's Guide, W. H. Freeman, NY, pp. 280–307 (1992), and Kaspczak et al., *Biochemistry* 28:9230–8 (1989).

VII. An Antibody Based Method and Kit for Detecting ALK-7

The present invention encompasses a method of detecting an ALK-7 polypeptide in a sample, comprising: (a) contacting the sample with an above-described antibody, under conditions such that immunocomplexes form, and (b) detecting the presence of said antibody bound to the polypeptide. In detail, the methods comprise incubating a test sample with one or more of the antibodies of the present invention and assaying whether the antibody binds to the test sample. Altered levels, either an increase or decrease, of ALK-7 in a sample as compared to normal levels may indicate disease.

Conditions for incubating an antibody with a test sample vary. Incubation conditions depend on the format employed in the assay, the detection methods employed, and the type and nature of the antibody used in the assay. One skilled in the art will recognize that nay one of the commonly available immunological assay formats (such as radioimmunoassays, enzyme-linked immunosorbent assays, diffusion based Ouchterlony, or rocket immunofluorescent assays) can readily be adapted to employ the antibodies of the present invention. Examples of such assays can be found in Chard, "An Introduction to Radioimmunoassay and Related Techniques" Elsevier Science Publishers, Amsterdam, The Netherlands (1986); Bullock et al., "Techniques in Immunocytochemistry," Academic Press, Orlando, Fla. Vol. 1 (1982), Vol. 2 (1983), Vol. 3 (1985); Tijssen, "Practice and Theory of Enzyme Immunoassays: Laboratory Techniques in Biochemistry and Molecular Biology," Elsevier Science Publishers, Amsterdam, The Netherlands (1985).

The immunological assay test samples of the present invention include cells, protein or membrane extracts of cells, or biological fluids such as blood, serum, plasma, or urine. The test sample used in the above-described method will vary based on the assay format, nature of the detection method and the tissues, cells or extracts used as the sample to be assayed. Methods for preparing protein extracts or membrane extracts of cells are well known in the art and can be readily be adapted in order to obtain a sample which is capable with the system utilized.

A kit contains all the necessary reagents to carry out the previously described methods of detection. The kit may comprise: (I) a first container means containing an above-described antibody, and (ii) second container means containing a conjugate comprising a binding partner of the antibody and a label. In another preferred embodiment, the kit further comprises one or more other containers comprising one or more of the following: wash reagents and reagents capable of detecting the presence of bound antibodies.

Examples of detection reagents include, but are not limited to, labeled secondary antibodies, or in the alternative, if the primary antibody is labeled, the chromophoric, enzymatic, or antibody binding reagents which are capable of reacting with the labeled antibody. The compartmentalized kit may be as described above for nucleic acid probe kits. One skilled in the art will readily recognize that the antibodies described in the present invention can readily be incorporated into one of the established kit formats which are well known in the art.

VIII. Isolation of Natural Binding Partners of ALK-7

The present invention also relates to a method of detecting natural binding partners capable of binding to an ALK-7 polypeptide. A natural binding partner of ALK-7 may be, for example, a ligand capable of binding to the extracellular domain of ALK-7 and stimulating ALK-7 activity. A natural binding partner may also be an intracellular protein that is part of the signaling cascade. The binding partner(s) may be present within a complex mixture, for example, serum, body fluids, or cell extracts.

In general methods for identifying natural binding partners comprise incubating a substance with ALK-7 and detecting the presence of a substance bound to ALK-7. Preferred methods include the two-hybrid system of Field and Song (supra), which is useful for identifying intracellular binding partners, and co-immunoprecipitation, which can be used to identify both intracellular and extracellular binding partners.

IX. Identification of and Uses for Substances Capable of Modulating ALK-7 Activity The present invention also relates to a method of detecting a substance capable of modulating ALK-7 activity. Such substances can either enhance activity (agonists) or inhibit activity (antagonists). Agonists and antagonists can be peptides, antibodies, products from natural sources such as fungal or plant extracts or small molecular weight organic compounds. In general, small molecular weight organic compounds are preferred. Examples of classes of compounds that can be tested for ALK-7 modulating activity are, for example but not limited to, oxindolines (see for example co-pending U.S. application Ser. Nos. 60/031,587; 60/031,588), thiazoles (co-pending U.S. application Ser. Nos. 60/033,522, 08/660,900), and naphthopyrones (U.S. Pat. No. 5,602,171).

In general the method comprises incubating cells that produce ALK-7 in the presence of a test substance and detecting changes in the level of ALK-7 activity or ALK-7 binding partner activity. A change in activity may be manifested by increased or decreased phosphorylation of the receptor complex, increased or decreased phosphorylation of an ALK-7 substrate, or increased or decreased biological response in cells. Biological responses can include, for example, proliferation, differentiation, neurite outgrowth, neurotransmitter release, or motility. The substance thus identified would produce a change in activity indicative of the agonist or antagonist nature of the substance. Once the substance is identified it can be isolated using techniques well known in the art, if not already available in a purified form.

The present invention also encompasses a method of agonizing (stimulating) or antagonizing ALK-7 associated activity in a mammal comprising administering to said mammal an agonist or antagonist to ALK-7 in an amount sufficient to effect said agonism or antagonism. Also encompassed in the present application is a method of treating diseases in a mammal with an agonist or antagonist of ALK-7-related activity comprising administering the agonist or antagonist to a mammal in an amount sufficient to agonize or antagonize ALK-7 associated function(s). The particular compound can be administered to a patient either by itself or in a pharmaceutical composition where it is mixed with suitable carriers or excipient(s). In treating a patient a therapeutically effective does of the compound is administered. A therapeutically effective dose refers to that amount of the compound that results in amelioration of symptoms or a prolongation of survival in a patient.

Toxicity and therapeutic efficacy of such compounds can be determined by standard pharmaceutical procedures in cell cultures or experimental animals. For example, for determining the $LD_{50}$ (the does lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized.

For any compound used in the method of the invention, the therapeutically effective dose can be estimated initially from cell culture assays. For example, a dose can be formulated in animal models to achieve a circulating plasma concentration range that includes the $IC_{50}$ as determined in a cell culture (i.e., the concentration of the test compound which achieves a half-maximal disruption of the protein complex, or a half-maximal inhibition of the cellular level and/or activity of a complex component). Such information can be used to more accurately determine useful doses in humans. Levels in plasma may be measured, for example, by HPLC.

The exact formulation, route of administration and dosage can be chosen by the individual physician in view of the patient's condition. (See e.g. Fingl et al., 1975, in "The Pharmacological Basis of Therapeutics," CH. 1 p. 1).

It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated does in the management of the oncogenic disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific conditions being treated, such agents may be formulated and administered systemically or locally. Techniques for formulation and administration may be found in "Remington's Pharmaceutical Sciences," 1990, 18th ed., Mack Publishing Co., Easton, Pa. Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

For injection, the agents of the invention may be formulated in aqueous solutions, preferably in physiologically compatible buffers such as Hanks's solution, Ringer's solution, or physiological saline buffer. Fur such transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosage suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, small organic molecules may be directly administered intracellularly.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

X. Transgenic Animals

Also contemplated by the invention are transgenic animals useful for the study of ALK-7 activity in complex in vivo systems. A variety of methods are available for the production of transgenic animals associated with this invention. DNA sequences encoding ALK-7 can be injected into the pronucleus of a fertilized egg before fusion of the male and female pronuclei, or injected into the nucleus of an embryonic cell (e.g., the nucleus of a two-cell embryo) following the initiation of cell division (Brinster, et al., *Proc. Nat. Acad. Sci. USA* 82:4438, 1985). Embryos can be infected with viruses, especially retroviruses, modified to carry inorganic-ion receptor nucleotide sequences of the invention.

Pluripotent stem cells derived from the inner cell mass of the embryo and stabilized in culture can be manipulated in culture to incorporate nucleotide sequences of the invention. A transgenic animal can be produced from such cells through implantation into a blastocyst that is implanted into a foster mother and allowed to come to term. Animals suitable for transgenic experiments can be obtained from standard commercial coursed such as Charles River (Wilmington, Mass.), Taconic (Germantown, N.Y.), Harlan Sprague Dawley (Indianapolis, Ind.), etc.

The procedures for manipulation of the rodent embryo and for microinjection of DNA into the pronucleus of the zygote are well known to those of ordinary skill in the art (Hogan, et al., supra). Microinjection procedures for fish, amphibian eggs and birds are detailed in Houdebine and Chourrout, Experientia 47: 897–905, 1991). Other procedures for introduction of DNA into tissues of animals are described in U.S. Pat. No. 4,945,050 (Sandford et al., Jul. 30, 1990).

By way of example only, to prepare a transgenic mouse, female mice are induced to superovulate. After being allowed to mate, the females are sacrificed by $CO_2$ asphyxiation or cervical dislocation and embryos are recovered from excised oviducts. Surrounding cumulus cells are removed. Pronuclear embryos are then washed and stored until the time of injection. Randomly cycling adult female mice are paired with vasectomized males. Recipient females are mated at the same time as donor females. Embryos then are transferred surgically. The procedure for generating transgenic rats is similar to that of mice. See Hammer, et al., *Cell* 63:1099–1112, 1990).

Methods for the culturing of embryonic stem (ES) cells and the subsequent production of transgenic animals by the introduction of DNA into ES cells using methods such as electroporation, calcium phosphate/DNA precipitation and direct injection also are well known to those of ordinary skill in the art. See, for example, Teratocarcinomas and Embryonic Stem Cells, A Practical Approach, E. J. Robertson, ed., IRL Press, 1987).

In cases involving random gene integration, a clone containing the sequence(s) of the invention is co-transfected with a gene encoding resistance. Alternatively, the gene encoding neomycin resistance is physically linked to the sequence(s) of the invention. Transfection and isolation of desired clones are carried out by any one of several methods well known to those of ordinary skill in the art (E. J. Robertson, supra).

DNA molecules introduced into ES cells can also be integrated into the chromosome through the process of homologous recombination. Capecchi, Science 244:1288–1292 (1989). Methods for positive selection of the recombination event (i.e., neo resistance) and dual positive-negative selection (i.e., neo resistance and gancyclovir resistance) and the subsequent identification of the desired clones by PCR have been described by Capecchi, supra and Joyner et al., *Nature* 338:153–156, 1989), the teachings of which are incorporated herein. The final phase of the procedure is to inject targeted ES cells into blastocysts and to transfer the blastocysts into pseudopregnant females. The resulting chimeric animals are bred and the offspring are analyzed by Southern blotting to identify individuals that carry the transgene. Procedures for the production of non-rodent mammals and other animals have been discussed by others. See Houdebine and Chourrout, supra; Pursel, et al., *Science* 244:1281–1288, 1989); and Simms, et al., *Bio/Technology* 6:179–183, 1988).

Thus, the invention provides transgenic, nonhuman mammals containing a transgene encoding an ALK-7 polypeptide or a gene effecting the expression of an ALK-7 polypeptide. Such transgenic nonhuman mammals are particularly useful as an in vivo test system for studying the effects of introducing a ALK-7 polypeptide, regulating the expression of a ALK-7 polypeptide (i.e., through the introduction of additional genes, antisense nucleic acids, or ribozymes).

A "transgenic animal" is an animal having cells that contain DNA which has been artificially inserted into a cell which DNA becomes part of the genome of the animal which develops from that cell. Preferred transgenic animals are primates, mice, rats, cows, pigs, horses, goats, sheep, dogs and cats. The transgenic DNA may encode for a human ALK-7 polypeptide. Native expression in an animal may be reduced by providing an amount of anti-sense RNA or DNA effective to reduce expression of the receptor.

XI. Gene Therapy

ALK-7 or its genetic sequences, both mutated and non-mutated, will also be useful in gene therapy (reviewed in Miller, *Nature* 357:455–460, (1992). Miller states that advances have resulted in practical approaches to human gene therapy that have demonstrated positive initial results. The basic science of gene therapy is described in Mulligan, *Science* 260:926–931, (1993).

In one preferred embodiment, an expression vector containing an ALK-7 coding sequence or an ALK-7 mutant coding sequence as described above is inserted into cells, the cells are grown in vitro and then infused in large numbers into patients. In another preferred embodiment, a DNA segment containing a promoter of choice (for example a strong promoter) is transferred into cells containing an endogenous ALK-7 in such a manner that the promoter segment enhances expression of the endogenous ALK-7 gene (for example, the promoter segment is transferred to the cell such that it becomes directly linked to the endogenous ALK-7 gene).

The gene therapy may involve the use of an adenovirus containing ALK-7 cDNA targeted to an appropriate cell type, systemic ALK-7 increase by implantation of engineered cells, injection with ALK-7 virus, or injection of naked ALK-7 DNA into appropriate cells or tissues, for example neurons.

Expression vectors derived from viruses such as retroviruses, vaccinia virus, adenovirus, adeno-associated virus, herpes viruses, several RNA viruses, or bovine papilloma virus, Amylin be used for delivery of nucleotide sequences (e.g., cDNA) encoding recombinant ALK-7 protein into the targeted cell population (e.g., tumor cells or neurons). Methods which are well known to those skilled in the art can be used to construct recombinant viral vectors containing coding sequences. See, for example, the techniques described in Maniatis et al., Molecular cloning: A Laboratory Manual, Cold Spring Harbor Laboratory, N.Y. (1989), and in Ausubel et al., Current Protocols in Molecular Biology, Greene Publishing Associates and Wiley Interscience, N.Y. (1989). Alternatively, recombinant nucleic acid molecules encoding protein sequences can be used as naked DNA or in reconstituted system eg., liposomes or other lipid systems for delivery to target cells (see e.g., Felgner et al., *Nature* 337:387–8, 1989). Several other methods for the direct transfer of plasmid DNA into cells exist for use in human gene therapy and involve targeting the DNA to receptors on cells by complexing the plasmid DNA to proteins. See, Miller, supra.

In its simplest form, gene transfer can be performed by simply injecting minute amounts of DNA into the nucleus of a cell, through a process of microinjection. (Capecchi M R, *Cell* 22:479–88), 1980). Once recombinant genes are introduced into a cell, they can be recognized by the cells normal mechanisms for transcription and translation, and a gene product will be expressed. Other methods have also been attempted for introducing DNA into larger numbers of cells. These methods include: transfection, wherein DNA is precipitated with $CaPO_4$ and taken into cells by pinocytosis (Chen C. and Okayama H, *Mol. Cell Biol.* 7:2745–52, 1987); electroporation, wherein cells are exposed to large voltage pulses to introduce holes into the membrane (Chu G., et al., *Nucleic Acids Res.*, 15:1311–26, 1987); lipofection/ liposome fusion, wherein DNA is packaged into lipophilic vesicles which fuse with a target cell (Felgner P L., et al., *Proc. Natl. Acad. Sci. USA.* 84:7413–7, 1987)); and particle bombardment using DNA bound to small projectiles (Yang N. S. et al., *Proc. Natl. Acad. Sci., USA* 87:9568–72, 1990). Another method for introducing DNA into cells is to couple the DNA to chemically modified proteins.

It has also been shown that adenovirus proteins are capable of destabilizing endosomes and enhancing the uptake of DNA into cells. The admixture of adenovirus to solutions containing DNA complexes, or the binding of DNA to polylysine covalently attached to adenovirus using protein crosslinking agents substantially improves the uptake and expression of the recombinant gene. Curiel D. T. et al., *Am. J. Respir. Cell. Mol. Biol.*, 6:247–52, 1992).

As used herein "gene transfer" means the process of introducing a foreign nucleic acid molecule into a cell. Gene transfer is commonly performed to enable the expression of a particular product encoded by the gene. The product may include a protein, polypeptide, anti-sense DNA or RNA, or enzymatically active RNA. Gene transfer can be performed in cultured cells or by direct administration into animals.

Generally gene transfer involves the process of nucleic acid contact with a target cell by non-specific or receptor mediated interactions, uptake of nucleic acid into the cell through the membrane or by endocytosis, and release of nucleic acid into the cytoplasm from the plasma membrane or endosome. Expression may require, in addition, movement of the nucleic acid into the nucleus of the cell and binding to appropriate nuclear factors for transcription.

As used herein "gene therapy" is a form of gene transfer and is included within the definition of gene transfer as used herein and specifically refers to gene transfer to express a therapeutic product from a cell in vivo or in vitro. Gene transfer can be performed ex vivo on cells which are then transplanted into a patient, or can be performed by direct administration of the nucleic acid or nucleic acid-protein complex into the patient.

In another preferred embodiment, a vector having nucleic acid sequences encoding an ALK-7 is provided in which the nucleic acid sequence is expressed only in specific tissue. Methods of achieving tissue-specific gene expression as set forth in International Publication No. WO 93/09236, filed Nov. 3, 1992 and published May 13, 1993.

In all of the preceding vectors set forth above, a further aspect of the invention is that the nucleic acid sequence contained in the vector may include additions, deletions or modifications to some or all of the sequence of the nucleic acid, as defined above.

In another preferred embodiment, a method of gene replacement is set forth. "Gene replacement" as used herein means supplying a nucleic acid sequence which is capable of being expressed in vivo in an animal and thereby providing or augmenting the function of an endogenous gene which is missing or defective in the animal.

XII. Compounds that Modulate the Function of ALK-7 Proteins

In an effort to discover novel treatments for diseases, biomedical researchers and chemists have designed, synthesized, and tested molecules that inhibit the function of protein kinases. Some small organic molecules form a class of compounds that modulate the function of protein kinases. Examples of molecules that have been reported to inhibit the function of protein kinases include, but are not limited to, bis monocyclic, bicyclic or heterocyclic aryl compounds (PCT WO 92/20642, published Nov. 26, 1992 by Maguire et al.), vinylene-azaindole derivatives (PCT WO 94/14808, published Jul. 7, 1994 by Ballinari et al.), 1-cyclopropyl-4-pyridyl-quinolones (U.S. Pat. No. 5,330,992), styryl compounds (U.S. Pat. No. 5,217,999), styryl-substituted pyridyl compounds (U.S. Pat. No. 5,302,606), certain quinazoline derivatives (EP Application No. 0 566 266 A1), seleoindoles and selenides (PCT WO 94/03427, published Feb. 17, 1994 by Denny et al.), tricyclic polyhydroxylic compounds (PCT WO 92/21660, published Dec. 10, 1992 by Dow), and benzylphosphonic acid compounds (PCT WO 91/15495, published Oct. 17, 1991 by Dow et al). The compounds that can traverse cell membranes and are resistant to acid hydrolysis are potentially advantageous therapeutics as they can become highly bioavailable after being administered orally to patients. However, many of these protein kinase inhibitors only weakly inhibit the function of protein kinases. In addition, many inhibit a variety of protein kinases and will therefore cause multiple side-effects as therapeutics for diseases.

Some indolinone compounds, however, form classes of acid resistant and membrane permeable organic molecules. WO 96/22976, published Aug. 1, 1996 by Ballinari et al. describes hydrosoluble indolinone compounds that harbor tetralin, naphthalene, quinoline, and indole substituents fused to the oxindole ring. These bicyclic substituents are in turn substituted with polar moieties including hydroxylated alkyl, phosphate, and ether moieties. U.S. patent application Ser. Nos. 08/702,232, filed Aug. 23, 1996, entitled "Indolinone Combinatorial Libraries and Related Products and Methods for the Treatment of Disease" by Tang et al. (Lyon & Lyon Docket No. 221/187) and 08/485,323, filed Jun. 7, 1995, entitled "Benzylidene-Z-Indoline Compounds for the Treatment of Disease" by Tang et al. and International Patent Publication WO 96/22976, published Aug. 1, 1996 by Ballinari et al., all of which are incorporated herein by reference in their entirety, including any drawings, describe indolinone chemical libraries of indolinone compounds harboring other bicyclic moieties as well as monocyclic moieties fused to the oxindole ring. Applications Ser. No. 08/702,232, filed Aug. 23, 1996, entitled "Indolinone Combinatorial Libraries and Related Products and Methods for the Treatment of Disease" by Tang et al., Ser. No. 08/485,323, filed Jun. 7, 1995, entitled "Benzylidene-Z-Indoline Compounds for the Treatment of Disease" by Tang et al., and WO 96/22976, published Aug. 1, 1996 by Ballinari et al. teach methods of indolinone synthesis, methods of testing the biological activity of indolinone compounds in cells, and inhibition patterns of indolinone derivatives.

Other examples of substances capable of modulating ALK-7 activity include, but are not limited to, tyrphostins, quinazolines, quinoxolines, and quinolines.

The quinazolines, tyrphostins, quinolines, and quinoxolines referred to above include well known compounds such as those described in the literature. For example, representative publications describing quinazoline include Barker et al., EPO Publication No. 0 520 722 A1; Jones et al., U.S. Pat. No. 4,447,608; Kabbe et al., U.S. Pat. No. 4,757,072; Kaul and Vougioukas, U.S. Pat. No. 5,316,553; Kreighbaum and Comer, U.S. Pat. No. 4,343,940; Pegg and Wardleworth, EPO Publication No. 0 562 734 A1; Barker et al., *Proc. of Am. Assoc. for Cancer Research* 32:327 (1991); Bertino, J. R., *Cancer Research* 3:293–304 (1979); Bertino, J. R., *Cancer Research* 9(2 part 1):293–304 (1979); Curtin et al., *Br. J. Cancer* 53:361–368 (1986); Fernandes et al., *Cancer Research* 43:1117–1123 (1983); Ferris et al. *J. Org. Chem.* 44(2):173–178; Fry et al., *Science* 265:1093–1095 (1994); Jackman et al., *Cancer Research* 51:5579–5586 (1981); Jones et al. *J. Med. Chem.* 29(6):1114–1118; Lee and Skibo, *Biochemistry* 26(23):7355–7362 (1987); Lemus et al., *J. Org. Chem.* 54:3511–3518 (1989); Ley and Seng, *Synthesis* 1975:415–522 (1975); Maxwell et al., *Magnetic Resonance in Medicine* 17:189–196 (1991); Mini et al., *Cancer Research* 45:325–330 (1985); Phillips and Castle, *J. Heterocyclic Chem.* 17(19):1489–1596 (1980); Reece et al., *Cancer Research* 47(11):2996–2999 (1977); Sculier et al., *Cancer Immunol. and Immunother.* 23:A65 (1986); Sikora et al., *Cancer Letters* 23:289–295 (1984); Sikora et al., *Analytical Biochem.* 172:344–355 (1988); all of which are incorporated herein by reference in their entirety, including any drawings.

Quinoxaline is described in Kaul and Vougioukas, U.S. Pat. No. 5,316,553, incorporated herein by reference in its entirety, including any drawings.

Quinolines are described in Dolle et al., *J. Med. Chem.* 37:2627–2629 (1994); MaGuire, *J. Med. Chem.* 37:2129–2131 (1994); Burke et al., *J. Med. Chem.* 36:425–432 (1993); and Burke et al. *BioOrganic Med. Chem. Letters* 2:1771–1774 (1992), all of which are incorporated by reference in their entirety, including any drawings.

Tyrphostins are described in Allen et al., *Clin. Exp. Immunol.* 91:141–156 (1993); Anafi et al., *Blood* 82:12:3524–3529 (1993); Baker et al., *J. Cell Sci.* 102:543–555 (1992); Bilder et al., *Amer. Physiol. Soc.* pp. 6363–6143:C721–C730 (1991); Brunton et al., *Proceedings of Amer. Assoc. Cancer Rsch.* 33:558 (1992); Bryckaert et al., *Experimental Cell Research* 199:255–261 (1992); Dong et al., *J. Leukocyte Biology* 53:53–60 (1993); Dong et al., *J. Immunol.* 151(5):2717–2724 (1993); Gazit et al., *J. Med. Chem.* 32:2344–2352 (1989); Gazit et al., "*J. Med. Chem.* 36:3556–3564 (1993); Kaur et al., *Anti-Cancer Drugs* 5:213–222 (1994); Kaur et al., King et al., *Biochem. J.* 275:413–418 (1991); Kuo et al., *Cancer Letters* 74:197–202 (1993); Levitzki, A., *The FASEB J.* 6:3275–3282 (1992); Lyall et al., *J. Biol. Chem.* 264:14503–14509 (1989); Peterson et al., *The Prostate* 22:335–345 (1993); Pillemer et al., *Int. J. Cancer* 50:80–85 (1992); Posner et al., *Molecular Pharmacology* 45:673–683 (1993); Rendu et al., *Biol. Pharmacology* 44(5):881–888 (1992); Sauro and Thomas, *Life Sciences* 53:371–376 (1993); Sauro and Thomas, *J. Pharm. and Experimental Therapeutics* 267(3):119–1125 (1993); Wolbring et al., *J. Biol. Chem.* 269(36):22470–22472 (1994); and Yoneda et al., *Cancer Research* 51:4430–4435 (1991); all of which are incorporated herein by reference in their entirety, including any drawings.

Other compounds that could be used as modulators include oxindolinones such as those described in U.S. patent application Ser. No. 08/702,232 filed Aug. 23, 1996, incorporated herein by reference in its entirety, including any drawings.

EXAMPLES

The examples below are non-limiting and are merely representative of various aspects and features of the present invention.

Dominant negative and constitutively active forms of ALK-7 are useful for delineating biologic consequences of either ablation or activation of this putative serine/threonine kinase. Generation of these reagents is facilitated by the strong conservation among members of the STK receptor family and knowledge of how such constructs have been made for homologues of ALK-7. An adenovirus expression system will allow expression of recombinant ALK-7 constructs in primary neuronal cells in order to determine if ALK-7 plays a role in processes such as neuronal survival or proliferation, neurite outgrowth, axon guidance, neurotransmitter regulation or synaptic modulation.

Example 1

Isolation and Characterization of ALK-7

In order to isolate ALK-7, we designed degenerate oligonucleotides encoding amino acid motifs within kinase subdomains II and VI common to all known mammalian STK receptors. (Hanks and Hunter, FASEB J. 9:576–595, 1995) Subdomain II is at the N-terminus of the kinase domain and contains the invariant lysine residue that is essential for enzyme activity and is involved in ATP binding by interacting with the a- and b-phosphates of all kinases whose structure has been elucidated. Subdomain VI is referred to as the catalytic loop and contains the consensus motif HRDLKXXN (SEQ ID NO:3). The Asp residue is involved in accepting the proton from the hydroxyl group during the phosphotransfer process key to all protein kinases. Based on comparison of all STK receptors, we designed degenerate oligonucleotide primers to these subdomains that would recognize both type I and type II STK receptors.

When this PCR strategy was applied to a human neuroblastoma cell line (SY5Y) sscDNA as a template, multiple copies of a novel DNA fragment (ALK-7) were isolated that exhibited significant homology to other STK receptors. The novel sequence was most similar to ALK-4 (Franzen, et al., Cell 75(4):681, 1993) and ALK-5 (ten Dijke, et al., Oncogene 8(10):2879, 1993) and was referred to as ALK-7.

Materials and Methods

Total RNAs were isolated using the Guanidine Salts/Phenol extraction protocol of Chomczynski and Sacchi (P. Chomczynski and N. Sacchi, Anal. Biochem. 162, 156 (1987) from normal human tissues, from regional sections of human brain, from cultured human tumor cell lines, and from primary neonatal rat sympathetic, motor, and sensory neuronal cells, as well as mesothalamic dopaminergic neurons.

These RNAs were used as templates to generate single-stranded cDNAs using the Superscript Preamplification System for First Strand Synthesis kit purchased from GibcoBRL (Life Technologies, U.S.A.; Gerard, G F et al. (1989), FOCUS 11, 66) under conditions recommended by manufacturer. A typical reaction used 10 ug total RNA or 2 ug poly(A)$^+$ RNA with 1.5 ug oligo(dT)$_{12-18}$ in a reaction volume of 60 uL. The product was treated with RNaseH and diluted to 100 uL with $H_2O$. For subsequent PCR amplification, 1–4 uL of these sscDNAs were used in each reaction.

Oligonucleotides were synthesized on an Applied Biosystems 394 DNA synthesizer using established phosphoramidite chemistry and were used unpurified after precipitation with ethanol. The degenerate oligonucleotide primers are:

STK1=5'-GARRARGT6GC6GT6AARRT6TT-3' (SEQ ID NO:4) (sense)

STK3-=5'-TTRATRTC6CKRTG6GM6AT6GM6GGYTT-3' (SEQ ID NO:5) (antisense).

These primers were derived from the peptide sequences E(K/E)VAVK(V/I)F (SEQ ID NO:6) (sense strand from kinase subdomain II) and KP(A/S)I(A/S)HRDIK (SEQ ID NO:7) (antisense strand from kinase subdomain VI), respectively. Degenerate nucleotide residue designations are: N=A, C, G, or T; R=A or G; Y=C or T; M=A or C; K=G or T; and 6=Inosine. Using ALK1 as a template, these primers produce a product of 321 bp.

A PCR reaction was performed using primers STK1 and STK3- applied to the single-stranded sources listed above. The primers were added at a final concentration of 5 uM each to a mixture containing 10 mM Tris HCl (pH8.3), 50 mM KCl, 1.5 mM $MgCl_2$, 200 uM each deoxynucleoside triphosphate, 0.001% gelatin, and 1.5 U AmpliTaq DNA Polymerase (Perkin-Elmer/Cetus), and 1–4 uL CDNA. Following 3 min denaturation at 95° C., the cycling conditions were 94° C. for 30 s, 37° C. for 1 min, a 2 min ramp to 72° C., and 72° C. for 1 min for the first 3 cycles, followed by 94° C. for 30 s, 50° C. for 1 min, and 72° C. for 1 min 45 s for 35 cycles. PCR fragments migrating at ~320 bp were isolated from 2% agarose gels using GeneClean (Bio101), and T-A cloned into the pCRII vector (Invitrogen Corp. U.S.A.) according to the manufacturer's protocol.

Colonies were selected from mini plasmid DNA-preparations using Qiagen columns and the plasmid DNAs were sequenced using cycle sequencing dye-terminator kit with AmpliTaq DNA Polymerase, FS (ABI, Foster City, Calif.). Sequencing reaction products were run on an ABI Prism 377 DNA Sequencer, and analyzed using the BLAST alignment algorithm (Altschul, S. F. et al., J. Mol. Biol. 215:403–10). A novel clone (STKR6.22) was isolated by PCR with primers STK1 and STK3- on single-stranded cDNA from human SY5Y cells as a template. This clone was subsequently designated as a fragment of human ALK-7.

A lambda gt11 (Clontech, Palo Alto, Calif.) cDNA library was constructed using mRNA from a pool of nine whole human pituitary glands. Phage were screened on nitrocellulose filters with the random primed $^{32}$P-labeled insert from STKR6.22 encoding human ALK-7 at 2×10$^6$ cpm/mL in hybridization buffer containing 6×SSC, 1×Denhardt's reagent, 0.1% SDS, with 0.1 mg/mL denatured, fragmented salmon sperm DNA. After overnight hybridization at 65° C., filters were washed in 0.1×SSC, 0.1% SDS at 65° C. Full length cDNA clones were sequenced on both strands using manual sequencing with T7 polymerase and oligonucleotide primers (Tabor and Richardson, 1987, Proc. Natl. Acad. Sci., USA 84: 4767–71).

Results

Two overlapping cDNA clones (P6 and P7), spanning 1794 nucleotides were isolated from a human pituitary library. This sequence contains an ATG at position 156 that conforms to the Kozak consensus for translational initiation and is followed by a 1,482 nucleotide open reading frame with the capacity to encode a polypeptide of 493 amino acids. There are no other initiation codons 5' to the ATG located at position 156. The coding region for human ALK-7 is flanked by 5' and 3' untranslated regions of 155 and 157, respectively. There is no polyadenylated region although the 3' end of the sequence shown in SEQ ID NO:1 is noticeably AT-rich, a feature characteristic of sequences from 3'-untranslated regions. An additional cDNA clone (P4) extended an additional 1 kb 3' of this sequence.

DNA sequence determination was performed with dideoxy terminators using Sequenase 2.0. A primer walking strategy on both strands was used to confirm the complete nucleotide sequence. Oligonucleotide primers were made with an ABI 348 DNA synthesizer.

A Smith-Waterman search with the human ALK-7 gene sequence of the public nonredundant nucleic acid and EST databases revealed no identical matching sequences confirming that this is a novel human gene. The closest match to the human ALK-7 sequence (85% nucleic acid identity) is a recent entry (GenBank ACC:U69702) which appears to be the rat orthologue of human ALK-7.

The 493 amino acid human ALK-7 sequence contains two hydrophobic regions from 1–25 and 114–138. (See SEQ ID NO:2) The first hydrophobic region meets the criteria of a signal peptide domain, with a discriminant score of 5.76 using the method of McGeoch (D. J. McGeoch, Virus Research, 3, 271, 1985), and with a weight matrix score of +6.75 (threshold=3.5) using the von Heijne algorithm (G. von Heijne, Nucl. Acids Res., 14, 4683, 1986). The second hydrophobic region generates a likelihood score of −9.34, using the ALOM method of Klein et al. (P. Klein, M. Kanehisa, and C. DeLisi, Diochim. Biophys. Acta, 815, 468, 1985) to predict transmembrane domains. This algorithm predicts a maximal range of the transmembrane domain to be from aa 108–138.

Based on this analysis, ALK-7 is predicted to be a type Ia integral membrane protein with a molecular weight of 52.35 kD after cleavage of the N-terminal signal peptide.

Example 2

Expression OF ALK-7

Using both Northern blots and PCR analysis with the novel fragment originally cloned from SY5Y cells as described above as a probe, we screened RNAs using from a large number of tumor cell lines and multiple human tissues, demonstrating an apparent selectivity in expression of ALK-7 in neuronal cells from the pituitary and substantiate nigra.

Materials and Methods

Northern Blot Analysis

Northern blots were obtained from Clontech (Palo Alto, Calif.) containing 2 ug polyA+ RNA from 16 different adult human tissues (spleen, thymus, prostate, testis, ovary, small intestine, colonic mucosa, heart, brain, placenta, lung, liver, skeletal muscle, kidney, pancreas, and peripheral blood leukocytes), and four different human fetal tissues (brain, lung, liver, and kidney), on a charge-modified nylon membrane. Additional Northern blots were prepared by running 20 ug total RNA on formaldehyde 1.2% agarose gel and transferring to nylon membranes.

Filters were hybridized with random prime [$^{32}$P]dCTP-labeled probes synthesized from the 320 bp insert from human ALK-7 clone STKR6.22. Hybridization was performed at 60° C. overnight in 6×SSC, 0.1% SDS, 1×Denhardt's solution, 100 mg/mL denatured herring sperm DNA with 1–2×10$^6$ cpm/mL of $^{32}$P-labeled DNA probes. The filters were washed in 0.1×SSC/0.1% SDS, 65° C., and exposed overnight on Kodak XAR-2 film.

Semi-Quantitative RT-PCR Detection

The expression pattern of ALK-7 was also investigated using a PCR technique, RNA was isolated from a variety of human cell lines, fresh frozen tissues, and primary tumors as detailed above. Single stranded cDNA was synthesized from 10 ug of each RNA as described above using the Superscript Preamplification System (GibcoBRL) These single strand templates were then used in a 35 cycle PCR reaction with two human ALK-7-specific oligonucleotides:

ALK-7a: 5'-AACTTTGGCTGGTATCTGAATATC-3' (SEQ ID NO:8), and

ALK-7b: 5'-CCTTGTGTACCAACAATCTCCATA-3' (SEQ ID NO:9).

Reaction products were electrophoresed on 2% agarose gels, stained with ethidium bromide and photographed on a UV light box. The relative intensity of the –150-bp ALK-7-specific bands were estimated for each sample. A similar pair of oligonucleotides was designed for detection of rat ALK-7:

4076: 5'-CTCCAGAGATGAGAGATCTTGG-3' (SEQ ID NO:10), and

4077: 5'-TTCCAGCCACGGTCACTATGTT-3') (SEQ ID NO:11), encompassing a ~210 bp region of the rat gene.

Results

ALK-7 mRNA transcript was not detectable by Northern analysis from multiple human tissue sources, suggesting its expression is highly restricted. Using a more sensitive PCR-based detection, ALK-7 was found to be expressed in human substantia nigra, anterior pituitary, and Calu-6 lung carcinoma cell line (see below). Weak expression was found in several other locations including whole brain, cerebellum, and prostate. Multiple other normal human tissues and tumor cell lines showed no detectable ALK-7 expression.

HUMAN ALK-7 RNA EXPRESSION ANALYSIS

| Medium (++) | Negative |
| --- | --- |
| Substantia Nigra | IMR-32 (neuroblastoma) |
| Anterior Pituitary | SY5Y (neuroblastoma) |
| Calu-6 (Lung Ca) | SK-N-SH (neuroblastoma) |
| | SWI763 (astrocytoma) |
| | SW1388 (astrocytoma) |
| Weak (+) | U-138 (glioblastoma) |
| | |
| | U87MG (glioblastoma) |
| Brain | Menirigiomas (1° tumors) |
| Posterior Pituitary | SKOV-3 (ovarian Ca) |
| Cerebellum | ASPC (pancreas Ca) |
| Ovary | CAPAN-1 (pancreas Ca) |
| Prostate | HS766T (pancreas Ca) |
| Fetal Intestine | PANC (pancreas Ca) |
| Duodenum | HOS (osteoSarcoma) |
| T48 (colon Ca) | KHOS (osteoSarcoma) |
| | HTB227 (breast Ca) |
| | HTB131 (breast Ca) |
| | LS123 (colon Ca) |
| | LS147T (colon Ca) |
| | SkCO4 (colon Ca) |
| | SW11E (colon Ca) |
| | HTC15 (colon Ca) |
| | SW403 (colon Ca) |
| | HT29 (colon Ca) |
| | SW627 (colon Ca) |
| | SW948 (colon Ca) |
| | HUVEC (h. endothelial) |
| | Fibroblasts (Primary) |
| | Pancreas |
| | Testis |
| | Thymus |
| | Liver |
| | Heart |
| | Placenta |
| | Lung |
| | Skel. Muscle |
| | Kidney |
| | Spleen |
| | Ovary |
| | Colon |
| | Leukocytes |

In situ Expression Profile of Rat ALK-7

The neuronal expression of ALK-7 was assessed by in situ analysis in sagittal and coronal sections from neonatal and adult rat brains using a fragment of the extracellular domain of rat ALK-7 as a probe. This region was selected because of its dissimilarity with the related ALK-4 and ALK-5. Other groups have performed in situ analyses with the catalytic domain of rat ALK-7 demonstrating specific expression in neuronal tissues (cerebellum, hippocampus, and brainstem nuclei), kidney, testis, lung, dorsolateral and anterior prostate, and adipose tissue. However, the probe used in these studies contained an ALK-7 catalytic domain which may cross-react with the related ALK-4 and ALK-5 (77% nucleotide sequence identity with stretches of 27/29 and 25/26 bp identity to rat ALK-7) and thereby broaden the expression profile. Using a more selective ALK-7 probe our analysis revealed the more restricted expression. In sagital sections, a moderate strength granular band was visible in the CA2 and CA3 regions of the hippocampus, dentate dyrus, olfactory tubercle, dorsal outer layer of the cortex, and in a band crossing the frontal cortex area 2 from the exterior to the corpus callosum. A moderate signal was detected in the caudate putamen and thalamic nuclei. In addition, signals of moderate strength were detected in the region of the magnocellular nucleus of the lateral hypothalamus and the medial tuberal nucleus. A similar signal was observed in the region of the cuneiform nucleus on the anterior border of the cerebellum. The cerebellum was devoid of hybridizing ALK-7.

Coronal sections support the finding of expression in the CA2, CA3 region of the hippocampus, dentate gyrus, caudate putamen, and in the region underlying the exterior of the cortex. In addition, a signal of moderate strength was detected in the dorsomedial part of the ventromedial hypothalamic nucleus. A dispersed nuclei signal of lesser strength was detected in the area of the amygdalopiriform transition.

Example 3

ALK-7-specific Antibodies

ALK-7-specific immunoreagents were raised in rabbits against KLH-conjugated synthetic peptide YRKKKRPN-VEEPL (SEQ ID NO:12) from the juxtamembrane portion of the cytoplasmic domain of ALK-7. This region is unique to ALK-7 compared to other type I STK receptors, thereby allowing for the generation of ALK-7 specific antisera. The N-terminal extracellular domain of ALK-7 expressed as a GST-fusion was also used as an immunogen to raise polyclonal antibodies in rabbits and to generate monoclonal antibodies in mice using the techniques described above. These antibodies were used to localize expression of the endogenous and recombinant protein as describe below.

Example 4

Recombinant ALK-7 Expression

The following example describes the construction of vectors for transient and stable expression in mammalian cells. Expression constructs were generated to make wild type ALK-7 as well as a signaling incompetent ALK-7 (ALK-7DN) and a constitutively activated ALK-7 (ALK-7TA).
Materials and Methods
Construction of Vectors Expression constructs were generated by PCR-assisted mutagenesis in which the entire coding domain of ALK-7 was tagged at its carboxy-terminal ends with the hemophilus influenza hemaglutinin (HA) epitope YPYDVPDYAS (SEQ ID NO:13) (Pati, *Gene* 114:285, 1992). This constructs were introduced into two mammalian expression vectors: pAdRSVOES-, a modified adenovirus vector for the generation of virus producing recombinant protein, and pRK5 for transient expression analysis.

Recombinant adenoviruses were generated by in vivo ligation as follows.

The transfer vector used contains the following DNA sequences in order: The left terminal region of adenovirus type 5 encoding the packaging sequences (adenovirus type 5 nucleotides 1–454); the Rous Sarcoma Virus long terminal repeat promoter and the SV40 polyA region, isolated as an expression cassette from the plasmid pREP (Invitrogen Corporation); nucleotides 3320–5790 of the type 5 adenoviral genome; and the ori and beta-lactamase genes derived from the *E. coli* plasmid pBluescript. Two additional forms of the plasmid were generated. The first, pAdRSVlacZ, was prepared by the insertion of a double stranded synthetic oligonucleotide into the BamHI restriction site between the RSV promotor and the SV40 polyA sequence with the following nucleotide sequence (upper strand shown): 5° CTTCGAAAGCTTGAAATCGGTACCATCGATTC-TAGAG TTAACTTCGAA (SEQ ID NO:14). The *E. coli* lacZ gene was excised from the expression plasmid pCMVb (Clontech, Inc.) with the enzyme Not I and inserted into the Not I site between the promoter and the polyA sequence. This generated a plasmid that expressed the lacZ gene, and had two BstBI restriction sites between the lacZ gene and the polyA region. The second plasmid (pAdRSVOES- ) was generated by inserting a double stranded synthetic oligonucleotide into the same region as above. Its nucleotide sequence was the following: 5' CTCTAGAACGCGTTAAGGCGCGCCAATATCGATGA-ATTCTTCGAAGC (SEQ ID NO:15). This plasmid allowed the introduction of exogenous cDNAs into the plasmid for expression purposes.

The viral DNA used for generation of recombinant viruses was derived from a virus (AdlacZBstBI) in which the left end of the adenovirus genome has been replaced by the homologous region of pAdRSVlacZ. To achieve this, DNA was isolated from the Ad5 dl327 strain of adenovirus (Jones and Shenk, *Cell*, 1978) (deleted in the E3 region), cleaved with ClaI enzyme, and cotransfected into the HEK2934 cell line via calcium phosphate coprecipitation with the pAdRS-VlacZ plasmid. Recombinant adenovirus plaques resulting from this transfection were screened for the ability to express the lacZ gene by histochemical staining with X-Gal. The resulting recombinant adenovirus, AdlacZBstBI, provided the backbone for additional adenovirus constructs, allowing a screen for recombinant plaques based on the presence or absence of lacZ activity in that further recombination would replace the lacZ gene with the cotransfected cDNA. To achieve this, the transfer vector construct is linearized by digestion with BstBI, and cotransfected with AdlacZBstBI DNA which has also been cleaved with BstBI. Typically, 5 mg of transfer vector plasmid DNA are coprecipitated with 2 mg of viral DNA for the transfection; in vivo ligation of viral DNA and linearized transfer vector produces a novel recombinant virus directing expression of the new transgene.

A signaling incompetent ALK-7 construct was also made in both vectors pAdRSVOES- and pRK5 by insertion of an HA-tag at aa 230 in the ALK-7 coding region just after catalytic domain II. Truncation of other TypeI STKRs in an analogous location has functioned in a dominant negative manner. This construct was called ALK-7DN. A constitutively active form of ALK-7 was generated by a Thr to Asp mutation at amino acid 194 just upstream of the catalytic domain I GXGXXG motif. In other Type I STKRs, this residue undergoes ligand-dependent trans-phosphorylation by the associated Type II STKR, resulting receptor activation and initiation of a signaling cascade. A similar mutation in other Type I STKR's results in a ligand-independent, constitutively activated receptor. This construct was called ALK-7TD.
Generation of Recombinant ALK-7—Adenovirus Early passage HEK293 cells (Graham, et al., *J. Gen. Virol.* 36:59, 1977) were maintained in Dulbecco's modified Eagles medium+10% calf serum. HEK293 monolayers were transfected with the ALK-7-encoding transfer vectors and cultured from five to seven days to allow plaques to appear. The monolayers were then stained with 25 mg/mL 5-bromo-4-chloro-3-indolyl-b-D-galactopyranoside for several hours to identify non-recombinant (blue-stained) plaques. Putative recombinant plaques were screened for expression of the transgene by infection of HEK293 cultures followed by immunohistochemistry with the monoclonal antibody recognizing the HA epitope. Viruses which were positive for transgene protein expression were picked and subjected to several rounds of claque purification prior to amplification and purification on cesium chloride gradients. Banded viruses were diluted five-fold with dilution buffer (Curiel et al., *Proc. Natl. Acad. Sci., USA* 88:8850–8854, 1991) and stored at −80° C. Approximate titers of the virus preparations were determined immunohistochemically on HEK293 cultures. The following viruses were generated: AdRSVALK-7-HA; AdRSVALK-7-DN; and AdRSVALK-7-TD.

Transient Expression

The pRK5 expression plasmids (10 ug DNA/100 mm plate) containing the KA-tagged ALK-7, the ALK-7DN, and ALK-7TD constructs were introduced into COS and 293 cells with lipofectamine (Gibco BRL). After 72 hours, the cells were harvested in 0.5 mL solubilization buffer (20 mM HEPES pH7.35, 150 mM NaCl, 10% glycerol, 1% Triton X-100, 1.5 mM $MgCl_2$, 1 mM EGTA, 2 mM phenylmethylsulfonyl fluoride, 1 µg/mL aprotinin). Sample aliquots were resolved by SDS polyacrylamide gel electrophoresis (PAGE) on 15% acrylamide/0.5% bis-acrylamide gels and electrophoretically transferred to nitrocellulose. Non-specific binding was blocked by preincubating blots in Blotto (phosphate buffered saline containing 5% w/v non-fat dried milk and 0.2% v/v nonidet P-40 (Sigma)), and recombinant protein was detected using a murine Mab to the HA decapeptide tag. Alternatively, recombinant protein can be detected using various ALK-7-specific antisera.

Expression in Neuronal Cells

The recombinant ALK-7 protein described above were expressed in PC12 cells and primary rat neuronal cultures by adenovirus mediated infection. These cells will allow further investigation into ALK-7 function. Recombinant protein expression was confirmed by immunostaining with an anti-HA antibody.

PC12 cultures (Greene, et al., *Methods Enzymol.* 147:207, 1987) were maintained in RPMI medium containing 10% horse serum and 5% fetal calf serum. Four differentiation experiments the medium was changed to RPMI containing 1×N2 supplement and 0.1% BSA, and the cells were grown on a collagen I substrate. For PC12 cell survival, the cells were grown in RPMI containing 0.1% BSA. All cultures also contained 1× penicillin/streptomycin. For adenoviral infections, PC12 cells were incubated overnight with recombinant viruses at a multiplicity of infection (MOI) between 1 and 10. The cells were then washed and replated either into differentiation or survival conditions for two days. Nerve Growth Factor (50 ng/mL) served as a positive control. For differentiation, the cultures were fixed with 2% paraformaldehyde and the percentage of cells bearing processes longer than 1 cell diameter was determined. For survival, the cultures were incubated with 0.05% MTT for 1.5 hours to stain living cells, and the relative number of cells surviving in each condition was determined.

Sympathetic and sensory neurons were isolated as described (Hawrot and Patterson, *Methods Enzymol.* 53:574, 1979; Fields et al., *Cell* 14:43, 1978) and cultured in a defined medium (Hawrot and Patterson, supra). Sympathetic neurons were isolated from superior cervical ganglia dissected from E20–E21 rat fetuses, while dorsal root ganglion sensory neurons were obtained from E16–E18 rats. The ganglia were treated with 0.25% trypsin for 10 minutes, washed, and triturated to obtain a single cell suspension. Sensory neurons were preplated for 1 hour on tissue culture plastic to deplete adherent cells. Dopaminergic neurons were isolated as described (Shimoda, et al., *Brain Research* 586:319–331, 1992) and cultured in Neurobasal medium, supplemented with B27 supplements (Life Technologies). Neurons were infected with adenoviruses for two hours on collagen I-coated tissue culture plastic (supplemented with NGF for sensory and sympathetic neurons), and the cells were then washed and allowed to recover for two to four additional hours (with NGF if appropriate). After the recovery period, the cells were washed extensively to remove the growth factor, and plated onto polylysine-laminin coated chamber slides. The addition of NGF at 50 ng/mL served as a positive control for survival of sensory and sympathetic neurons. After an additional two days to three days, the sensory and sympathetic cultures were stained with calcein AM (1 mg/mL) for 45 minutes, mounted and examined by immunofluorescence. Generally, five disperse fields representing 7% of the well were photographed and the number of surviving neurons quantitated. To determine dopaminergic neuron survival, the cultures were fixed and the number of tyrosine hydroxylase positive neurons was determined.

Results

Recombinant ALK-7 protein expressed in COS cells migrated with apparent Mr of 52 kD–63 kD, consistent with its predicted molecular weight of 54 kD based on its primary amino acid sequence and the presence of multiple glycosylation sites. The ALK-7TD constitutive active form produced proteins indistinguishable from the wild type construct on SDS-PAGE. The ALK-7DN construct expressed proteins of Mr 23.5 kd, 28 kD and 32 kD consistent with the presence of varying amounts of glycosylation on this truncated receptor. This analysis confirms the recombinant protein can be stably produced in mammalian cells.

Example 5

Screening Systems for the Identification of Inhibitors of ALK-7 Activity

Assays may be performed in vitro or in vivo and are described in detail herein or can be obtained by modifying existing assays, such as the growth assay described in patent application Ser. No. 08/487,088, filed Jun. 7, 1995, by Tang et al., and entitled "Novel Pharmaceutical Compounds," or the assays described in patent application Ser. No. 60/005,167, filed Oct. 13, 1995 by Seedorf et al., and entitled "Diagnosis and Treatment of TKA-1 related disorders," all of which are hereby incorporated herein by reference in their entirety including any drawings. Another assay which could be modified to use the genes of the present invention is described in International Application No. WO 94/23039, published Oct. 13, 1994, hereby incorporated herein by reference in its entirety including any drawings. Other possibilities include detecting kinase activity in an autophosphorylation assay or testing for kinase activity on standard substrates such as histones, myelin basic protein, gamma tubulin, or centrosomal proteins. Binding partners may be identified by putting the N-terminal portion of the protein into a two-hybrid screen or detecting phosphotyrosine of a dual specificity kinase (Fields and Song, U.S. Pat. No. 5,283,173, issued Feb. 1, 1994, incorporated by reference herein, including any drawings).

One skilled in the art would readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments, are exemplary, and are not intended as limitations on the scope of the invention. It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

In view of the degeneracy of the genetic code, other combinations of nucleic acids also encode the claimed peptides and proteins of the invention. For example, all four nucleic acid sequences GCT, GCC, GCA, and GCG encode the amino acid alanine. Therefore, if for an amino acid there exists an average of three codons, a polypeptide of 100 amino acids in length will, on average, be encoded by $3^{100}$, or $5 \times 10^{47}$, nucleic acid sequences. Thus, a nucleic acid sequence can be modified to form a second nucleic acid sequence, encoding the same polypeptide as encoded by the first nucleic acid sequences, using routine procedures and without undue experimentation. Thus, all possible nucleic acids that encode the claimed peptides and proteins are also fully described herein, as if all were written out in full taking into account the codon usage, especially that preferred in humans.

Furthermore, changes in the amino acid sequences of polypeptides, or in the corresponding nucleic acid sequence encoding such polypeptide, may be designed or selected to take place in an area of the sequence where the significant activity of the polypeptide remains unchanged. For example, an amino acid change may take place within a β-turn, away from the active site of the polypeptide. Also changes such as deletions (e.g. removal of a segment of the polypeptide, or in the corresponding nucleic acid sequence encoding such polypeptide, which does not affect the active site) and additions (e.g. addition of more amino acids to the polypeptide sequence without affecting the function of the active site, such as the formation of GST-fusion proteins, or additions in the corresponding nucleic acid sequence encoding such polypeptide without affecting the function of the active site) are also within the scope of the present invention. Such changes to the polypeptides can be performed by those with ordinary skill in the art using routine procedures and without undue experimentation. Thus, all possible nucleic and/or amino acid sequences that can readily be determined not to affect a significant activity of the peptide or protein of the invention are also fully described herein.

Other embodiments are within the following claims.

What is claimed is:

1. An isolated, enriched or purified nucleic acid molecule which comprises a nucleotide sequence that
   (a) encodes a polypeptide comprising the full length amino acid sequence set forth in SEQ ID NO:2; or
   (b) is completely complementary to the nucleotide sequence of (a).

2. The nucleic acid molecule of claim 1, wherein said nucleic acid molecule is isolated, enriched, or purified from a mammal.

3. The nucleic acid molecule of claim 1, further comprising a vector or promoter effective to initiate transcription in a host cell.

4. An isolated, enriched or purified nucleic acid molecule comprising a nucleotide sequence that
   (a) encodes a polypeptide comprising one or more of the following segments of amino acid residues of SEQ ID NO: 2: 26–113 and 193–485;
   (b) is completely complementary to the nucleotide sequence of (a).

5. An isolated, enriched or purified nucleic acid molecule comprising a nucleotide sequence that
   (a) encodes a polypeptide comprising one or more of the following domains of the amino acid sequence set forth in SEQ ID NO: 2: the extracellular region and the catalytic domain; or
   (b) is completely complementary to the nucleotide sequence of (a).

6. The nucleic acid molecule of claim 1, claim 4 or claim 5, further comprising a nucleotide sequence that encodes a second polypeptide, wherein said second polypeptide is fused to said polypeptide.

7. The nucleic acid molecule of claim 1, claim 4 or claim 5, wherein said nucleic acid molecule further encodes GST.

8. A cultured recombinant cell comprising an isolated, enriched or purified nucleic acid molecule encoding either the polypeptide according to claim 1, claim 4 or claim 5 or the polypeptide according to claim 1, claim 4 or claim 5 fused to an additional polypeptide.

9. An isolated, enriched or purified nucleic acid molecule comprising the nucleotide sequence set forth in SEQ ID NO:1.

10. The isolated, enriched or purified nucleic acid molecule of claim 1, claim 4 or claim 5, further comprising restriction endonuclease recognition sites at the 5' end and/or 3' end.

11. The nucleic acid molecule of claim 3, wherein said vector is selected from the group consisting of pBR322, pUC118, pUC119, ColE1, pSC101, pACYC 184, pVX, pC194, pC221, pT127, plJ101, BPV, vaccinia, SV40, 2-micron circle, λgt10, λgt11, and pMAM-neo.

12. The nucleic acid molecule of claim 3, wherein said promoter is selected from the group consisting of the int promoter of bacteriophage λ, the bla promoter of the β-lactamase gene sequence of pBR322, the CAT promoter of the chloramphenicol acetyl transferase gene sequence of pBR325, the major right or left promoters of bacteriophage λ, the trp, recA, lacZ, lacI or gal promoters of *E. coli* and the α-amylase or sigma-28 specific promoters of *B. subtilis*.

13. The nucleic acid molecule of claim 3, wherein said host cell is a yeast cell, a fungi cell, an insect cell, a plant cell or a mammalian cell.

14. The nucleic acid molecule of claim 13, wherein said mammalian cell is selected from the group consisting of a COS Cell, an HEK293 cell, a VERO cell, a 3T3 cell, a CHO-K1 cell, a 32D cell, an SP2/0 cell, a J558L cell, an IMR 332 cell and a PC12 cell.

15. The nucleic acid molecule of claim 3, wherein said host cell is eukaryotic, and wherein said promoter is selected from the group consisting of a mouse metallothionein I promoter, the TK promoter of Herpes virus, the SV40 early promoter and the yeast gal 4 promoter.

16. The nucleic acid molecule of claim 3, wherein said vector is pRK5.

17. An isolated, enriched or purified nucleic acid molecule comprising a nucleotide sequence that encodes a polypeptide comprising the amino acid sequence set forth in SEQ ID NO:2, except that (a) the cytoplasmic domain of said polypeptide is truncated and (b) relative to wild type ALK-7, said polypeptide is signaling incompetent and/or dominant negative.

18. The nucleic acid molecule of claim 17, wherein said polypeptide is truncated at position 230 of the amino acid sequence set forth in SEQ ID NO:2 and further characterized by the addition of a hemophilus influenza hemagglutinin-tag (HA-tag) at position 230 of the amino acid sequence set forth in SEQ ID NO:2.

19. An isolated, enriched or purified nucleic acid molecule encoding a constitutively active polypeptide, wherein said nucleic acid molecule comprises a nucleotide sequence that encodes a polypeptide comprising the full length amino acid sequence set forth in SEQ ID NO:2, except that said amino acid sequence contains an Asp at position 194 of SEQ ID NO:2 instead of a Thr.

* * * * *

SEQUENCE LISTING (1) GENERAL INFORMATION:

(iii) NUMBER OF SEQUENCES:    15

(2) INFORMATION FOR SEQ ID NO: 1:

(i) SEQUENCE CHARACTERISTICS:
       (A) LENGTH:     1793 base pairs
       (B) TYPE:       nucleic acid
       (C) STRANDEDNESS: single
       (D) TOPOLOGY:   linear (xi) SEQUENCE DESCRIPTION: SEQ ID NO: 1:

```
CGGCCACACT GACTAGAGCC AACCGCGCAC TTCAAAAGGG TGTCGGTGCC GCGCTCCCCT      60

CCCGCGGCCC GGGAACTTCA AAGCGGGCCG TGCTGCCCCG GCTGCCTCGC TCTGCTCTGG     120

GGCCTCGCAG CCCCGGCGCG GCCGCCTGGT GGCGATGACC CGGGCGCTCT GCTCAGCGCT     180

CCGCCAGGCT CTCCTGCTGC TCGCAGCGGC CGCCGAGCTC TCGCCAGGAC TGAAGTGTGT     240

ATGTCTTTTG TGTGATTCTT CAAACTTTAC CTGCCAAACA GAAGGAGCAT GTTGGGCATC     300

AGTCATGCTA ACCAATGGAA AAGAGCAGGT GATCAAATCC TGTGTCTCCC TTCCAGAACT     360

GAATGCTCAA GTCTTCTGTC ATAGTTCCAA CAATGTTACC AAAACCGAAT GCTGCTTCAC     420

AGATTTTTGC AACAACATAA CACTGCACCT TCCAACAGCA TCACCAAATG CCCCAAAACT     480

TGGACCCATG GAGCTGGCCA TCATTATTAC TGTGCCTGTT TGCCTCCTGT CCATAGCTGC     540
```

-continued

```
GATGCTGACA GTATGGGCAT GCCAGGGTCG ACAGTGCTCC TACAGGAAGA AAAAGAGACC    600

AAATGTGGAG GAACCACTCT CTGAGTGCAA TCTGGTAAAT GCTGGAAAAA CTCTGAAAGA    660

TCTGATTTAT GATGTGACCG CCTCTGGATC TGGCTCTGGT CTACCTCTGT TGGTTCAAAG    720

GACAATTGCA AGGACGATTG TGCTTCAGGA AATAGTAGGA AAAGGTAGAT TTGGTGAGGT    780

GTGGCATGGA AGATGGTGTG GGGAAGATGT GGCTGTGAAA ATATTCTCCT CCAGAGATGA    840

AAGATCTTGG TTTCGTGAGG CAGAAATTTA CCAGACGGTC ATGCTGCGAC ATGAAAACAT    900

CCTTGGTTTC ATTGCTGCTG ACAACAAAGA TAATGGAACT TGGACTCAAC TTTGGCTGGT    960

ATCTGAATAT CATGAACAGG GCTCCTTATA TGACTATTTG AATAGAAATA TAGTGACCGT   1020

GGCTGGAATG ATCAAGCTGG CGCTCTCAAT TGCTAGTGGT CTGGCACACC TTCATATGGA   1080

GATTGTTGGT ACACAAGGTA AACCTGCTAT TGCTCATCGA GACATAAAAT CAAAGAATAT   1140

CTTAGTGAAA AAGTGTGAAA CTTGTGCCAT AGCGGACTTA GGGTTGGCTG TGAAGCATGA   1200

TTCAATACTG AACACTATCG ACATACCTCA GAATCCTAAA GTGGGAACCA AGAGGTATAT   1260

GGCTCCTGAA ATGCTTGATG ATACAATGAA TGTGAATATC TTTGAGTCCT TCAAACGAGC   1320

TGACATCTAT TCTGTTGGTC TGGTTTACTG GGAAATAGCC CGGAGGTGTT CAGTCGGAGG   1380

AATTGTTGAG GAGTACCAAT TGCCTTATTA TGACATGGTG CCTTCAGATC CCTCGATAGA   1440

GGAAATGAGA AAGGTTGTTT GTGACCAGAA GTTTCGACCA AGTATCCCAA ACCAGTGGCA   1500

AAGTTGTGAA GCACTCCGAG TCATGGGGAG AATAATGCGT GAGTGTTGGT ATGCCAACGG   1560

AGCGGCCCGC CTAACTGCTC TTCGTATTAA GAAGACTATA TCTCAACTTT GTGTCAAAGA   1620

AGACTGCAAA GCCTAATGAT GATAATTATG TTAAAAAGAA ATCTCTCATA GCTTTCTTTT   1680

CCATTTTCCC CTTTATGTGA ATGTTTTTGC CATTTTTTTT TTGTTCTACC TCAAAGATAA   1740

GACAGTACAG TATTTAAGTG CCCATAAGGC AGCATGAAAA GATAACTCTA AAG          1793
```

(2) INFORMATION FOR SEQ ID NO: 2:

(i) SEQUENCE CHARACTERISTICS:
        (A) LENGTH: 493 amino acids
        (B) TYPE: amino acid
        (C) STRANDEDNESS: single
        (D) TOPOLOGY: linear (ii) MOLECULE TYPE: Peptide (xi) SEQUENCE DESCRIPTION: SEQ ID NO: 2:

```
Met Thr Arg Ala Leu Cys Ser Ala Leu Arg Gln Ala Leu Leu Leu
  1               5                  10                  15

Ala Ala Ala Glu Leu Ser Pro Gly Leu Lys Cys Val Cys Leu Leu
             20                  25                  30

Cys Asp Ser Ser Asn Phe Thr Cys Gln Thr Glu Gly Ala Cys Trp Ala
         35                  40                  45

Ser Val Met Leu Thr Asn Gly Lys Glu Gln Val Ile Lys Ser Cys Val
     50                  55                  60

Ser Leu Pro Glu Leu Asn Ala Gln Val Phe Cys His Ser Ser Asn Asn
 65                  70                  75                  80

Val Thr Lys Thr Glu Cys Cys Phe Thr Asp Phe Cys Asn Asn Ile Thr
                 85                  90                  95

Leu His Leu Pro Thr Ala Ser Pro Asn Ala Pro Lys Leu Gly Pro Met
            100                 105                 110

Glu Leu Ala Ile Ile Ile Thr Val Pro Val Cys Leu Leu Ser Ile Ala
            115                 120                 125
```

```
Ala Met Leu Thr Val Trp Ala Cys Gln Gly Arg Gln Cys Ser Tyr Arg
    130                 135                 140

Lys Lys Lys Arg Pro Asn Val Glu Glu Pro Leu Ser Glu Cys Asn Leu
145                 150                 155                 160

Val Asn Ala Gly Lys Thr Leu Lys Asp Leu Ile Tyr Asp Val Thr Ala
                165                 170                 175

Ser Gly Ser Gly Ser Gly Leu Pro Leu Leu Val Gln Arg Thr Ile Ala
            180                 185                 190

Arg Thr Ile Val Leu Gln Glu Ile Val Gly Lys Gly Arg Phe Gly Glu
        195                 200                 205

Val Trp His Gly Arg Trp Cys Gly Glu Asp Val Ala Val Lys Ile Phe
    210                 215                 220

Ser Ser Arg Asp Glu Arg Ser Trp Phe Arg Glu Ala Glu Ile Tyr Gln
225                 230                 235                 240

Thr Val Met Leu Arg His Glu Asn Ile Leu Gly Phe Ile Ala Ala Asp
                245                 250                 255

Asn Lys Asp Asn Gly Thr Trp Thr Gln Leu Trp Leu Val Ser Glu Tyr
            260                 265                 270

His Glu Gln Gly Ser Leu Tyr Asp Tyr Leu Asn Arg Asn Ile Val Thr
        275                 280                 285

Val Ala Gly Met Ile Lys Leu Ala Leu Ser Ile Ala Ser Gly Leu Ala
    290                 295                 300

His Leu His Met Glu Ile Val Gly Thr Gln Gly Lys Pro Ala Ile Ala
305                 310                 315                 320

His Arg Asp Ile Lys Ser Lys Asn Ile Leu Val Lys Lys Cys Glu Thr
                325                 330                 335

Cys Ala Ile Ala Asp Leu Gly Leu Ala Val Lys His Asp Ser Ile Leu
            340                 345                 350

Asn Thr Ile Asp Ile Pro Gln Asn Pro Lys Val Gly Thr Lys Arg Tyr
        355                 360                 365

Met Ala Pro Glu Met Leu Asp Asp Thr Met Asn Val Asn Ile Phe Glu
    370                 375                 380

Ser Phe Lys Arg Ala Asp Ile Tyr Ser Val Gly Leu Val Tyr Trp Glu
385                 390                 395                 400

Ile Ala Arg Arg Cys Ser Val Gly Gly Ile Val Glu Glu Tyr Gln Leu
                405                 410                 415

Pro Tyr Tyr Asp Met Val Pro Ser Asp Pro Ser Ile Glu Glu Met Arg
            420                 425                 430

Lys Val Val Cys Asp Gln Lys Phe Arg Pro Ser Ile Pro Asn Gln Trp
        435                 440                 445

Gln Ser Cys Glu Ala Leu Arg Val Met Gly Arg Ile Met Arg Glu Cys
    450                 455                 460

Trp Tyr Ala Asn Gly Ala Ala Arg Leu Thr Ala Leu Arg Ile Lys Lys
465                 470                 475                 480

Thr Ile Ser Gln Leu Cys Val Lys Glu Asp Cys Lys Ala
                485                 490
```

(2) INFORMATION FOR SEQ ID NO: 3:

(i) SEQUENCE CHARACTERISTICS:
        (A) LENGTH:        8 amino acids
        (B) TYPE:          amino acid
        (C) STRANDEDNESS:  single
        (D) TOPOLOGY:     linear

```
    (ii) MOLECULE TYPE:       Peptide (ix) FEATURE:
         (D) OTHER INFORMATION:    "Xaa" in positions 6 and 7 stand
             for an unspecified amino acid.

(xi) SEQUENCE DESCRIPTION: SEQ ID NO:  3:

His Arg Asp Leu Lys Xaa Xaa Asn
1               5

(2) INFORMATION FOR SEQ ID NO:  4:

(i) SEQUENCE CHARACTERISTICS:
         (A) LENGTH:         23 base pairs
         (B) TYPE:           nucleic acid
         (C) STRANDEDNESS:   single
         (D) TOPOLOGY:       linear (ix) FEATURE:
         (D) OTHER INFORMATION:    The letter "R" stands for A or G.
             The letter "N" stands for Inosine.

(xi) SEQUENCE DESCRIPTION: SEQ ID NO:  4:

GARRARGTNG CNGTNAARRT NTT                                           23

(2) INFORMATION FOR SEQ ID NO:  5:

(i) SEQUENCE CHARACTERISTICS:
         (A) LENGTH:         29 base pairs
         (B) TYPE:           nucleic acid
         (C) STRANDEDNESS:   single
         (D) TOPOLOGY:       linear (ix) FEATURE:
         (D) OTHER INFORMATION:    The letter "R" stands for A or G.
             The letter "N" stands for Inosine.
             The letter "K" stands for G or T.
             The letter "M" stands for A or C.
             The letter "Y" stands for C or T.

(xi) SEQUENCE DESCRIPTION: SEQ ID NO:  5:

TTRATRTCNC KRTGNGMNAT NGMNGGYTT                                     29

(2) INFORMATION FOR SEQ ID NO:  6:

(i) SEQUENCE CHARACTERISTICS:
         (A) LENGTH:         8 amino acids
         (B) TYPE:           amino acid
         (C) STRANDEDNESS:   single
         (D) TOPOLOGY:       linear (ii) MOLECULE TYPE:       Peptide (ix) FEATURE:
         (D) OTHER INFORMATION:    "Xaa" in position 2 stands for Lys
             or Glu. "Xaa" in position 7 stands for
             Val or Ile.

(xi) SEQUENCE DESCRIPTION: SEQ ID NO:  6:

Glu Xaa Val Ala Val Lys Xaa Phe
1               5

(2) INFORMATION FOR SEQ ID NO:  7:

(i) SEQUENCE CHARACTERISTICS:
         (A) LENGTH:         10 amino acids
         (B) TYPE:           amino acid
         (C) STRANDEDNESS:   single
         (D) TOPOLOGY:       linear (ii) MOLECULE TYPE:       Peptide
```

```
    (ix) FEATURE:
          (D) OTHER INFORMATION:  "Xaa" in position 3 stands for Ala
              or Ser.  "Xaa" in position 5 stands for Ala or Ser.

(xi) SEQUENCE DESCRIPTION: SEQ ID NO:  7:

Lys Pro Xaa Ile Xaa His Arg Asp Ile Lys
1               5                   10

(2) INFORMATION FOR SEQ ID NO:  8:

(i) SEQUENCE CHARACTERISTICS:
          (A) LENGTH:       24 base pairs
          (B) TYPE:         nucleic acid
          (C) STRANDEDNESS: single
          (D) TOPOLOGY:     linear (xi) SEQUENCE DESCRIPTION: SEQ ID NO:  8:

AACTTTGGCT GGTATCTGAA TATC                                              24

(2) INFORMATION FOR SEQ ID NO:  9:

(i) SEQUENCE CHARACTERISTICS:
          (A) LENGTH:       24 base pairs
          (B) TYPE:         nucleic acid
          (C) STRANDEDNESS: single
          (D) TOPOLOGY:     linear (xi) SEQUENCE DESCRIPTION: SEQ ID NO:  9:

CCTTGTGTAC CAACAATCTC CATA                                              24

(2) INFORMATION FOR SEQ ID NO:  10:

(i) SEQUENCE CHARACTERISTICS:
          (A) LENGTH:       22 base pairs
          (B) TYPE:         nucleic acid
          (C) STRANDEDNESS: single
          (D) TOPOLOGY:     linear (xi) SEQUENCE DESCRIPTION: SEQ ID NO:  10:

CTCCAGAGAT GAGAGATCTT GG                                                22

(2) INFORMATION FOR SEQ ID NO:  11:

(i) SEQUENCE CHARACTERISTICS:
          (A) LENGTH:       22 base pairs
          (B) TYPE:         nucleic acid
          (C) STRANDEDNESS: single
          (D) TOPOLOGY:     linear (xi) SEQUENCE DESCRIPTION: SEQ ID NO:  11:

TTCCAGCCAC GGTCACTATG TT                                                22

(2) INFORMATION FOR SEQ ID NO:  12:

(i) SEQUENCE CHARACTERISTICS:
          (A) LENGTH:       13 amino acids
          (B) TYPE:         amino acid
          (C) STRANDEDNESS: single
          (D) TOPOLOGY:     linear (ii) MOLECULE TYPE:     Peptide (xi) SEQUENCE DESCRIPTION: SEQ ID NO:  12:

Tyr Arg Lys Lys Lys Arg Pro Asn Val Glu Glu Pro Leu
1               5                   10
```

-continued (2) INFORMATION FOR SEQ ID NO: 13:

(i) SEQUENCE CHARACTERISTICS:
        (A) LENGTH:      10 amino acids
        (B) TYPE:        amino acid
        (C) STRANDEDNESS: single
        (D) TOPOLOGY:    linear (ii) MOLECULE TYPE:    Peptide (xi) SEQUENCE DESCRIPTION: SEQ ID NO: 13:

Tyr Pro Tyr Asp Val Pro Asp Tyr Ala Ser
1            5                     10

(2) INFORMATION FOR SEQ ID NO: 14:

(i) SEQUENCE CHARACTERISTICS:
        (A) LENGTH:      48 base pairs
        (B) TYPE:        nucleic acid
        (C) STRANDEDNESS: single
        (D) TOPOLOGY:    linear (xi) SEQUENCE DESCRIPTION: SEQ ID NO: 14:

CTTCGAAAGC TTGAAATCGG TACCATCGAT TCTAGAGTTA ACTTCGAA        48

(2) INFORMATION FOR SEQ ID NO: 15:

(i) SEQUENCE CHARACTERISTICS:
        (A) LENGTH:      47 base pairs
        (B) TYPE:        nucleic acid
        (C) STRANDEDNESS: single
        (D) TOPOLOGY:    linear (xi) SEQUENCE DESCRIPTION: SEQ ID NO: 15:

CTCTAGAACG CGTTAAGGCG CGCCAATATC GATGAATTCT TCGAAGC        47